(12) United States Patent
Watanabe et al.

(10) Patent No.: US 11,504,445 B2
(45) Date of Patent: Nov. 22, 2022

(54) PHOTOCATALYTIC AIR CLEANING STRUCTURE FOR AIR CLEANER, AIR CLEANER HAVING THE AIR CLEANING STRUCTURE, AND PHOTOCATALYTIC FILTER FOR USE IN THE AIR CLEANING STRUCTURE

(71) Applicant: APS Japan Co., Ltd., Osaka (JP)

(72) Inventors: Teruo Watanabe, Osaka (JP); Hidemitsu Watanabe, Osaka (JP); Hiroyuki Watanabe, Osaka (JP); Takafumi Watanabe, Osaka (JP)

(73) Assignee: APS JAPAN CO., LTD., Osaka (JP)

( * ) Notice: Subject to any disclaimer, the term of this patent is extended or adjusted under 35 U.S.C. 154(b) by 0 days.

(21) Appl. No.: 16/060,243

(22) PCT Filed: Dec. 9, 2016

(86) PCT No.: PCT/JP2016/086769
§ 371 (c)(1),
(2) Date: Jun. 7, 2018

(87) PCT Pub. No.: WO2017/099231
PCT Pub. Date: Jun. 15, 2017

(65) Prior Publication Data
US 2018/0344890 A1 Dec. 6, 2018

(30) Foreign Application Priority Data

Dec. 11, 2015 (JP) ............................. JP2015-242247
Feb. 22, 2016 (JP) ............................. JP2016-030601

(51) Int. Cl.
*A61L 9/20* (2006.01)
*F24F 13/28* (2006.01)
(Continued)

(52) U.S. Cl.
CPC ............. *A61L 9/205* (2013.01); *B01J 21/063* (2013.01); *B01J 35/004* (2013.01); *B01J 35/04* (2013.01);
(Continued)

(58) Field of Classification Search
CPC ..... A61L 9/00; A61L 9/18; A61L 9/20; A61L 9/205
(Continued)

(56) References Cited

U.S. PATENT DOCUMENTS 5,069,885 A * 12/1991 Ritchie ................. B01J 16/005
422/186
2002/0024278 A1 * 2/2002 Matsuda ................. H01J 61/40
313/112

(Continued)

FOREIGN PATENT DOCUMENTS

| JP | H11-314017 A | 11/1999 |
|---|---|---|
| JP | 2001-301451 A | 10/2001 |

(Continued)

OTHER PUBLICATIONS

Air Filters, Jan. 7, 2014, Home Depot Product Page, <http://www.homedepot.com/b/Heating-Venting-Cooling-Air-Filters/10-Premium/N-5yc1vZc4kwZ1z0uhdb> (Year: 2014).*

(Continued)

*Primary Examiner* — Jason L McCormack
(74) *Attorney, Agent, or Firm* — Kratz, Quintos & Hanson, LLP

(57) ABSTRACT

A photo catalytic filter is configured such that a plurality of plate-shaped members on which a photocatalyst is carried face each other with a gap therebetween, and the gaps form an air flow path. Each plate-shaped member has end surfaces respectively on an air entrance side and an air exit side of the gap. A UV irradiation unit faces the end surfaces on at least (Continued)

one of the air entrance side and the air exit side of the plate-shaped members, and is a predetermined distance away from those end surfaces. An air supply path for taking air from a lateral direction substantially parallel to the end surfaces, and supplying the air to the flow path, or an air discharge path for discharging the air exiting the flow path to a lateral direction substantially parallel to the end surfaces, is formed between the UV irradiation unit and the end surfaces of the plate-shaped members.

11 Claims, 34 Drawing Sheets

(51) Int. Cl.
    *B01J 21/06*     (2006.01)
    *B01J 35/00*     (2006.01)
    *B01J 35/04*     (2006.01)
    *F24F 8/22*     (2021.01)
    *F24F 8/167*     (2021.01)

(52) U.S. Cl.
    CPC ......... *F24F 13/28* (2013.01); *A61L 2209/111* (2013.01); *A61L 2209/12* (2013.01); *A61L 2209/14* (2013.01); *A61L 2209/16* (2013.01); *F24F 8/167* (2021.01); *F24F 8/22* (2021.01)

(58) Field of Classification Search
    USPC ............................................ 250/435, 455.11
    See application file for complete search history.

(56) References Cited

U.S. PATENT DOCUMENTS

2012/0171079 A1*   7/2012   Morito ................... B01J 21/063
                                                              502/5
2015/0224218 A1*   8/2015   Burnett ................... A61L 9/205
                                                              29/458

FOREIGN PATENT DOCUMENTS

| JP | 2003-93486 A | 4/2003 |
| --- | --- | --- |
| JP | 2004-49468 A | 2/2004 |
| JP | 2005-9784 A | 1/2005 |
| JP | 3150894 U | 6/2009 |
| JP | 2011-114894 A | 6/2011 |

OTHER PUBLICATIONS

International Search Report for International Application No. PCT/JP2016/086769 dated Feb. 7, 2017 (2 Sheets).

* cited by examiner

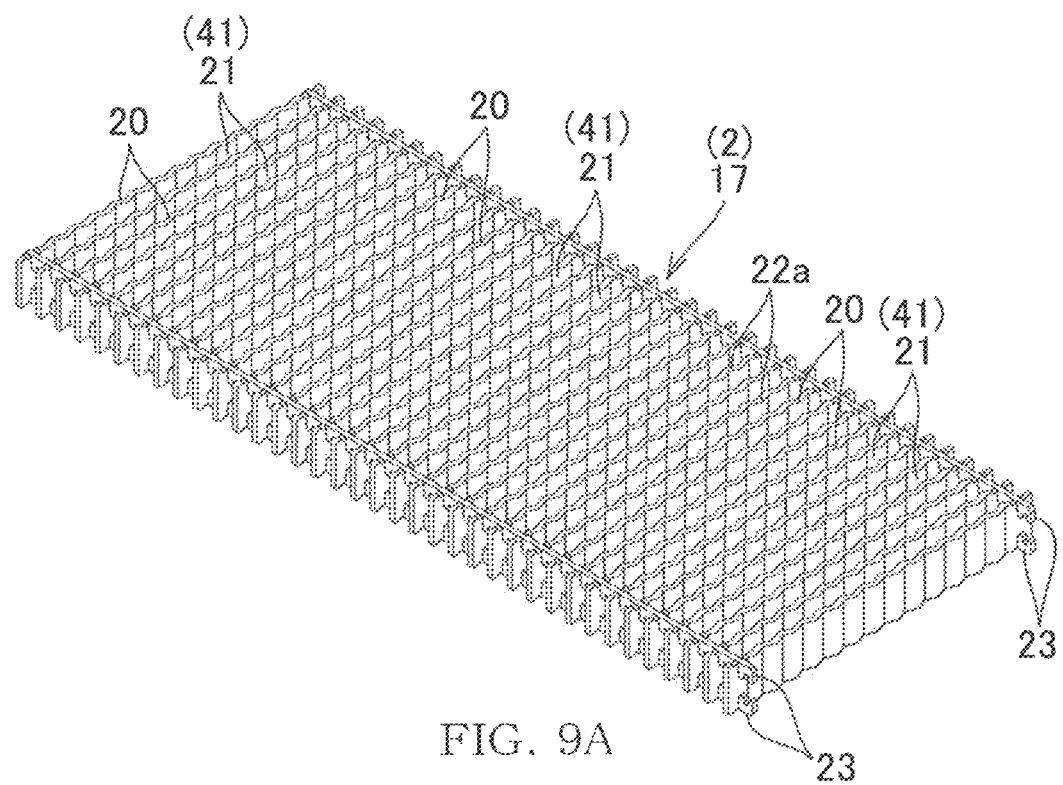
FIG. 9A
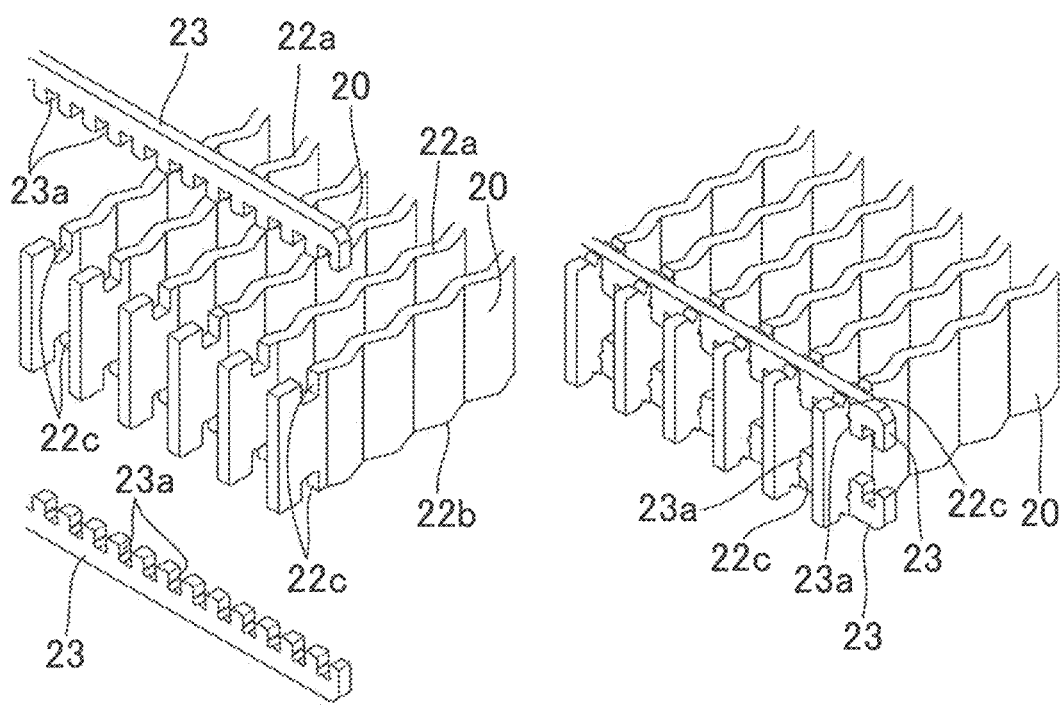
FIG. 9B
FIG. 9C

PHOTOCATALYTIC AIR CLEANING STRUCTURE FOR AIR CLEANER, AIR CLEANER HAVING THE AIR CLEANING STRUCTURE, AND PHOTOCATALYTIC FILTER FOR USE IN THE AIR CLEANING STRUCTURE

TECHNICAL FIELD

The present invention relates to a photocatalytic air cleaning structure for an air cleaner, an air cleaner having the structure, and a photocatalytic unit for use in the air cleaning structure.

BACKGROUND ART

Air cleaners having an air cleaning structure that decompose viruses, etc., using a photocatalyst have conventionally been proposed (see, for example, Patent Literature 1 and Patent Literature 2). Such a conventional photocatalytic air cleaning structure is provided with a photocatalytic filter unit that includes: a plate-shaped substrate that is provided with a large number of air passage pores penetrating the substrate in the thickness direction, and has the front and back surfaces, one of which carries a photocatalyst, such as titanium oxide; and a plurality of ultraviolet (UV) lamps that are positioned to face the photocatalyst carrying surface, and are spaced apart from each other. Air is supplied to the unit from one of the front and back sides of the unit, in the thickness direction, and is then passed through the air passage pores of the plate-shaped substrate, the photocatalyst layer, and the space between each UV lamp. Hazardous matter in air, when passing through the photocatalyst layer, is decomposed and removed by the photocatalyst that is excited with ultraviolet light.

However, in such a conventional photocatalytic filter, the plate-shaped substrate and the UV lamps are arranged in the thickness direction, and therefore, the unit itself has a great thickness. In addition, an air supply path and an air discharge path are provided on the front and back sides of the unit, and therefore, the air cleaner as a whole needs to be thick enough to accommodate these paths. This places a limit on a reduction in thickness or size. There is also a limit on an increase in the number of UV lamps because air is passed through the gaps between the UV lamps. There is also a certain limit on the maximum amount of ultraviolet light with which the photocatalyst of the plate-shaped substrate is irradiated, and the improvement of the irradiation efficiency. For example, even if the photocatalyst is extended and carried on deep portions of the inner surfaces of the air passage pores, it is difficult to efficiently irradiate the deep portions with ultraviolet light.

CITATION LIST

Patent Literature

[PTL 1] Japanese Utility Model Registration No. 3150894
[PTL 2] Japanese Unexamined Patent Application Publication (Translation of PCT Application) No. 2011-114894

SUMMARY OF THE INVENTION

Problems to be Solved by the Invention

In view of the above circumstances, the present invention provides a photocatalytic air cleaning structure that allows a photocatalyst carried on a substrate to be efficiently irradiated with ultraviolet light, and thereby further improves the air cleaning effect of the photocatalyst, and in addition, reduces an increase in the thickness of an entire air cleaner, which contributes to a reduction in thickness or size. The present invention also provides an air cleaner having the air cleaning structure, and a photocatalyst unit for use in the air cleaning structure.

Solution to the Problems

To achieve the above objects, the present invention provides a photocatalytic air cleaning structure for use in an air cleaner including: a photocatalytic filter that includes a plurality of plate-shaped members each having a front and a back surface carrying a photocatalyst and being arranged such that the front surface of one plate-shaped member faces the back surface of another plate-shaped member adjacent thereto with a gap being interposed therebetween, the gap defining an air flow path; and a UV irradiation unit that emits ultraviolet light toward the gap, and faces one of end surfaces of each of the plate-shaped members of the photocatalytic filter with a predetermined distance array from the one of the end surfaces, the end surfaces including an end surface on an air entrance side to the gap and an end surface on an air exit side from the gap, in which the UV irradiation unit and one of the end surfaces of the plate-shaped member are arranged so as to define therebetween: an air supply path for taking in air from a lateral direction substantially parallel to the one of the end surfaces, and supplying the air to the air flow path defined by the gap between the plate-shaped members; or an air discharge path for discharging the air exiting from the flow path to a lateral direction substantially parallel to the one of the end surfaces.

Here, each of the plate-shaped members of the photocatalytic filter preferably has a pair of short sides facing each other and a pair of long sides facing each other. The end surface on the air entrance side and the end surface on the air exit side are preferably the end surfaces corresponding to the pair of long sides of each of the plate-shaped members, thereby allowing air to pass through the air flow path in a direction in which the short sides of the plate-shaped members extend. The UV irradiation unit is preferably positioned to face the end surfaces corresponding to at least one of the pair of long sides of the plate-shaped member.

In addition, the air supply path or the air discharge path is preferably a flow path defined between the UV irradiation unit and the end surfaces on the at least one of the air entrance and exit sides of the plate-shaped members, the flow path allowing air to be taken from or discharged to a lateral direction which is substantially parallel to the end surfaces on the at least one of the air entrance and exit sides, and corresponds to a direction in which the end surfaces on the at least one of the air entrance and exit sides extend.

In addition, each of the plate-shaped members of the photocatalytic filter is preferably an undulating plate that alternately bends toward front and back of the plate, in a direction along which the end surfaces on the air entrance side or the end surfaces on the air exit side extend.

In addition, the UV irradiation unit is preferably positioned to face the end surface on the air exit side of the plate-shaped member of the photocatalytic filter, and a dust collection filter having a white or whitish color is preferably provided on the air entrance side of the photocatalytic filter so as to occlude an entrance of the air.

In particular, a photocatalyst is preferably carried by the dust collection filter.

In addition, the UV irradiation unit preferably includes: a substrate facing an entire of an air exit of the photocatalytic filter with a space being interposed therebetween, the space being the air discharge path; a UV light source provided on and attached to a surface of the substrate, which faces the photocatalytic filter, and for irradiating the gap between the plate-shaped members with ultraviolet light; and a light transmissive cover plate provided between the substrate and the photocatalytic filter. The air exiting from the gap between the plate-shaped members is preferably discharged through the space between the cover plate and the end surface on the air exit side of each of the plate-shaped members, along a surface of the cover plate, toward a lateral edge.

In addition, the photocatalytic filter preferably includes a linking member for linking the plate-shaped members together, and all the plate-shaped members are preferably integrated together into a unit arrangement by the linking member.

In the above photocatalytic air cleaning structure of the present invention, each of the plate-shaped members is preferably a metal plate.

The present invention also provides an air cleaner including the above photocatalytic air cleaning structure, in which, in a housing, the photocatalytic filter and the UV irradiation unit facing the photocatalytic filter are positioned and aligned with each other in a fore-and-aft direction of the housing. An air intake opening and an air discharge opening are each provided in an upper, a lower, a left, and a right peripheral wall for linking a front and a rear wall of the housing at a predetermined position. In the housing, the air supply path extending from the air intake opening to the air entrance of the photocatalytic filter, and an air discharge path extending from the air exit of the photocatalytic filter to the air discharge opening, are provided. A fan for forcing air to flow is provided in a middle of the air supply path or the air discharge path.

The present invention also provides a photocatalytic filter for use in the above air cleaning structure, including a metal filter base body that includes a metal plate body having a plurality of row-shaped crest portions and a plurality of row-shaped trough portions alternately formed, with a through groove extending in a row direction for allowint a fluid to pass through being provided in each of the crest portions and each of the trough portions; and a middle wall portion facing the through groove being the plate-shaped member, and a tube-shaped frame formed of synthetic resin into which the metal filter base body is fitted, in which the metal filter base body and the tube-shaped frame form a unit arrangement.

Advantageous Effects of the Invention

In the above air cleaning structure according to the present invention of the present application, a UV irradiation unit is provided a predetermined distance away from end surfaces on an air entrance or exit side of plate-shaped members of a photocatalytic filter. An air supply path for taking air from a lateral direction substantially parallel to the end surfaces, or an air discharge path for discharging the air to a lateral direction substantially parallel to the end surfaces, is formed between the UV irradiation unit and the end surfaces of the plate-shaped members. Thus, unlike the conventional art, air is not supplied or discharged through gaps between UV lamps, and the flexibility of design of the UV irradiation unit is significantly improved. Therefore, it is easy to more efficiently irradiate a photocatalyst on the plate-shaped members with ultraviolet light, and thereby significantly improve the air cleaning effect of the photocatalyst.

In addition, in the photocatalytic filter, the plurality of plate-shaped members, on the front and back surfaces of which the photocatalyst is carried, are arranged such that the front surface of one plate-shaped member faces the back surface of another plate-shaped member adjacent thereto with a gap being interposed therebetween, and the gaps form an air flow path. Therefore, ultraviolet light emitted from the UV irradiation unit can efficiently reach deep inside each gap. In addition, even in the case where air is taken into or discharged from a space between the UV irradiation unit and the end surfaces of the plate-shaped members, from or to a lateral direction, air can be passed through the gaps between the plate-shaped members without becoming stagnant, and during the passage, the air can be efficiently cleaned by the photocatalyst provided on the front and back surfaces of the plate-shaped members.

In addition, as described above, the present invention has the structure in which air is supplied from or discharged to a lateral direction of the gap between the UV irradiation unit and the photocatalytic filter, but not the structure in which air is passed through the UV irradiation unit. Therefore, unlike the conventional art, it is not necessary to provide an air supply path or an air discharge path on the opposite side of the UV irradiation unit from the base material that carries a photocatalyst, and therefore, the thickness of an entire air cleaner can be reduced, resulting in a reduction in thickness or size of the air cleaner.

In addition, each plate-shaped member of the photocatalytic filter has a pair of short sides facing each other and a pair of long sides facing each other. The end surface on the air entrance side and the end surface on the air exit side are the end surfaces corresponding to the pair of long sides facing each other of each plate-shaped member. As a result, the air flow path causes air to pass in a direction in which the short sides of the plate-shaped members extend. The UV irradiation unit is positioned to face the end surfaces corresponding to at least one of the pair of long sides of the plate-shaped members. Therefore, the area of the UV irradiation unit can be flexibly designed, so that the entire region extending in the long side direction can be efficiently irradiated with ultraviolet light. In addition, the depth direction of the gap between the plate-shaped members in which air flows is along the short side. Therefore, ultraviolet light more reliably reaches deep inside the gaps, whereby the air cleaning effect of the photocatalyst can be more reliably exerted.

In addition, the air supply path or the air discharge path is a flow path through which air is taken in from or discharged to a space between the UV irradiation unit and the end surfaces of the plate-shaped members, in a lateral direction which is substantially parallel to the end surfaces and in which the end surfaces extend. Therefore, air is taken in and discharged in a direction in which the gaps between the plate-shaped members extend, and is allowed to efficiently flow in the entire gaps between the plate-shaped members without resistance. As a result, air can be efficiently cleaned by the photocatalyst.

In addition, each plate-shaped member of the photocatalytic filter is an undulating plate that alternately bends toward the front and back of the plate, in a direction in which the end surfaces on the air entrance side or the end surfaces on the air exit side extend. Therefore, the area where air flowing in the gap comes into contact with the photocatalyst can be increased, so that the air cleaning effect can be improved. In addition, ultraviolet light entering from the UV irradiation unit into the gaps between the plate-shaped members is not interfered with, and is scattered by the bending portions, so that the supported photocatalyst can be efficiently irradiated with ultraviolet light from various directions, which can enhance the photocatalytic effect.

In addition, the UV irradiation unit is positioned to face the end surfaces on the air exit side of the plate-shaped members of the photocatalytic filter, and a dust collection filter having a white or whitish color is provided on the air entrance side of the photocatalytic filter, occluding the entrance. Therefore, a dust collection filter having substantially the same area as that of the front and back surfaces of the photocatalytic filter can be provided. Furthermore, ultraviolet light emitted from the UV irradiation unit to the gaps between the plate-shaped members of the photocatalytic filter is reflected by the white or whitish dust collection filter, so that the photocatalyst in the gaps is more efficiently irradiated.

In particular, because a photocatalyst is supported by the dust collection filter, dust, etc., captured by the dust collection filter and air passing in the dust collection filter can be cleaned by the photocatalytic effect.

In addition, in the present invention, as described above, air is not passed through the UV irradiation unit, and therefore, the flexibility of design is ensured. For example, the UV irradiation unit can include: a substrate facing the entire air exit of the photocatalytic filter with a gap being interposed therebetween, the gap being the air discharge path; a UV light source provided on and attached to a surface of the substrate facing the photocatalytic filter, and for irradiating the gaps between the plate-shaped members with ultraviolet light; and a light transmissive cover plate provided between the substrate and the photocatalytic filter. Air exiting the gaps between the plate-shaped members can be discharged through a gap between the cover plate and the end surfaces on the air exit side of the plate-shaped members, along a surface of the cover plate, toward a lateral edge. As a result, the gaps between the plate-shaped members of the photocatalytic filter can be efficiently irradiated with a large amount of ultraviolet light using the substrate provided with an efficient UV LED device as a light source, whereby the air cleaning function of the photocatalyst can be easily further enhanced. In addition, heat occurring in the UV irradiation unit can be efficiently removed by air flowing in the air discharge path. Furthermore, the cover plate prevents accumulation of dust, etc., on the substrate and the UV light source. In addition, dust, etc., accumulated on the cover plate can be easily removed by only cleaning the cover plate when the photocatalytic filter is maintained or replaced.

In addition, the photocatalytic filter includes a linking member for linking the plate-shaped members together, and all the plate-shaped members are integrated together into a unit arrangement by the linking member. Therefore, the photocatalytic filter can be easily replaced or maintained, resulting in an improvement in convenience. Such an integrated unit arrangement may, for example, be produced as follows. The plate-shaped members and the linking member may be produced as separate members using a metal material, a synthetic resin material, etc., and may be joined together. In particular, when the plate-shaped members and the linking member are formed of synthetic resin, the plate-shaped members and the linking member may be integrally formed by molding.

In addition, when the plate-shaped member is formed of a metal plate, the stiffness of the plate-shaped member can be maintained at a required level even if the plate-shaped member is thin. The thin plate-shaped members allow the gap between each plate-shaped member to form a wide flow path. As a result, the photocatalyst on the front and back surfaces of the plate-shaped members can be efficiently irradiated with ultraviolet light from the UV irradiation unit, whereby the air cleaning effect of the photocatalyst can be more reliably efficiently exerted.

In the air cleaner including the photocatalytic air cleaning structure according to the present invention, in a housing, the photocatalytic filter and a UV irradiation unit facing the photocatalytic filter are positioned and aligned with each other in a fore-and-aft direction of the housing. An air intake opening and an air discharge opening are each provided in an upper, a lower, a left, and a right peripheral wall for linking a front and a rear wall of the housing at a predetermined position. In the housing, an air supply path extending from the air intake opening to the air entrance of the photocatalytic filter, and an air discharge path extending from the air exit of the photocatalytic filter to the air discharge opening, are provided. A fan for forcing air to flow is provided in a middle of the air supply path or the air discharge path. Therefore, air taken into the air cleaner through the air intake opening provided in the upper, lower, left, and right peripheral walls at a predetermined position can be efficiently supplied to the photocatalytic filter having the air entrance and the air exit arranged in the fore-and-aft direction, through the air supply path. Air passing through the gaps between the plate-shaped members can be efficiently discharged in a lateral direction of the photocatalytic filter, through the air discharge path, and can then be discharged out of the air cleaner through the discharge opening provided in the upper, lower, left, and right peripheral walls at a predetermined position.

Therefore, the air cleaner can be configured to have a reduced thickness and size. In addition, it is not necessary to provide an air entrance/exit opening in the front or rear wall. Therefore, for example, the air cleaner can be used as a wall-mounted type to display pictures, photographs, liquid crystal screens, etc., on the front surface. Thus, the air cleaner can have various applications.

In addition, the photocatalytic filter of the present invention includes a unit arrangement including: a metal filter base body that includes a metal plate body having a plurality of row-shaped crest portions and a plurality of row-shaped trough portions alternately formed, with a through groove extending in a row direction for passing a fluid being provided in both the crest portions and the trough portions; and a middle wall portion facing the through groove being the plate-shaped member, and a tube-shaped frame formed of synthetic resin into which the metal filter base body is fitted. Therefore, the photocatalytic filter is easily replaced or maintained, resulting in an improvement in convenience. In addition, an undulating surface formed by the crest portions and the trough portions provides a large surface area where the photocatalytic filter comes into contact with air. Therefore, a catalyst layer formed on a surface of the middle wall portion is efficiently irradiated with ultraviolet light, whereby the photocatalytic effect is efficiently exerted.

BRIEF DESCRIPTION OF THE DRAWINGS

FIG. 9A is a perspective view showing a metal filter base body included in a photocatalytic filter, and FIGS. 9B and 9C are explanatory diagrams of a unit structure thereof.

DESCRIPTION OF EMBODIMENTS

Figure 1:
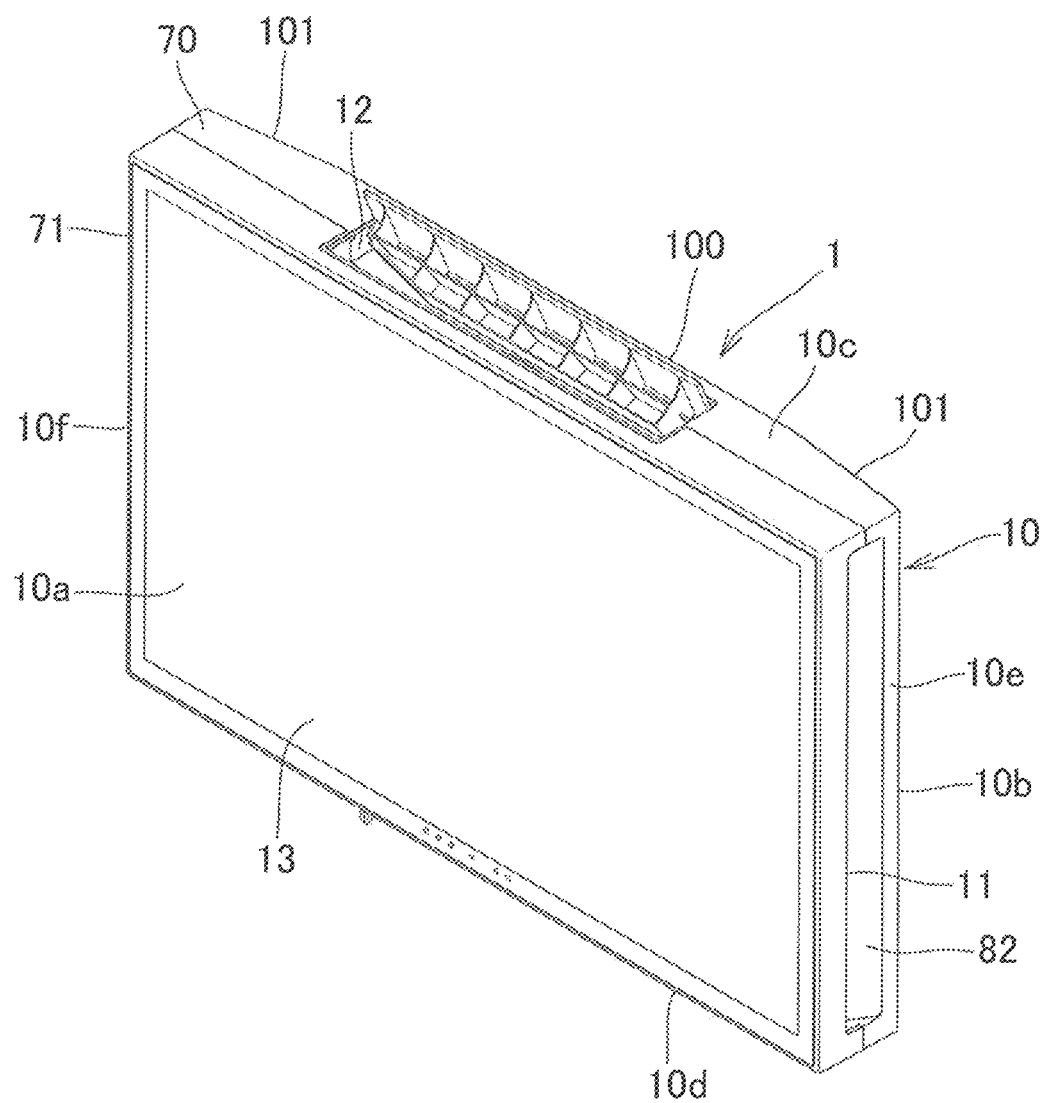
FIG. 1 is a perspective view showing an air cleaner according to a first embodiment of the present invention.

Next, embodiments of the present invention is described in detail with reference to the accompanying drawings. A first embodiment of the present invention is first described with reference to FIG. 1, FIG. 2, FIG. 3, FIG. 4, FIG. 5A, FIG. 5B, FIG. 6, FIG. 7, FIG. 8A, FIG. 8B, FIG. 9A, FIG. 9B, FIG. 9C, FIG. 10A, FIG. 10B, FIG. 11, FIG. 12A and FIG. 12B.

As shown in FIG. 1, FIG. 2, FIG. 3 and FIG. 4, an air cleaner 1 according to the first embodiment of the present invention is provided with an intake opening 11 through which air is taken into a housing 10, and a discharge opening 12 through which air is discharged out of the housing 10, in an upper, a lower, a left, and a right peripheral wall (an upper wall 10c, a lower wall 10d, a right wall 10e, and a left wall 10f) that link a front and a rear wall (a front wall 10a and a rear wall 10b) of the housing 10, at predetermined positions. In the housing 10, provided is an air cleaning structure S that includes one or more photocatalytic filters 2, and one or more UV irradiation units 3 that face the photocatalytic filters 2 and irradiate the photocatalytic filters 2 with ultraviolet light. The photocatalytic filter 2 is aligned with the UV irradiation unit 3 in the fore-and-aft direction, i.e., arranged one behind the other.

In this example, two photocatalytic filters 2 are provided on each of the left and right sides, i.e., a total of four photocatalytic filters 2 are provided. The two photocatalytic filters 2 on each of the left and right sides are flush with each other and are vertically linked together. A single UV irradiation unit 3, which includes a UV LED substrate, is provided on each of the left and right sides, facing the entire surfaces of the two (upper and lower) photocatalytic filters 2.

Figure 2:
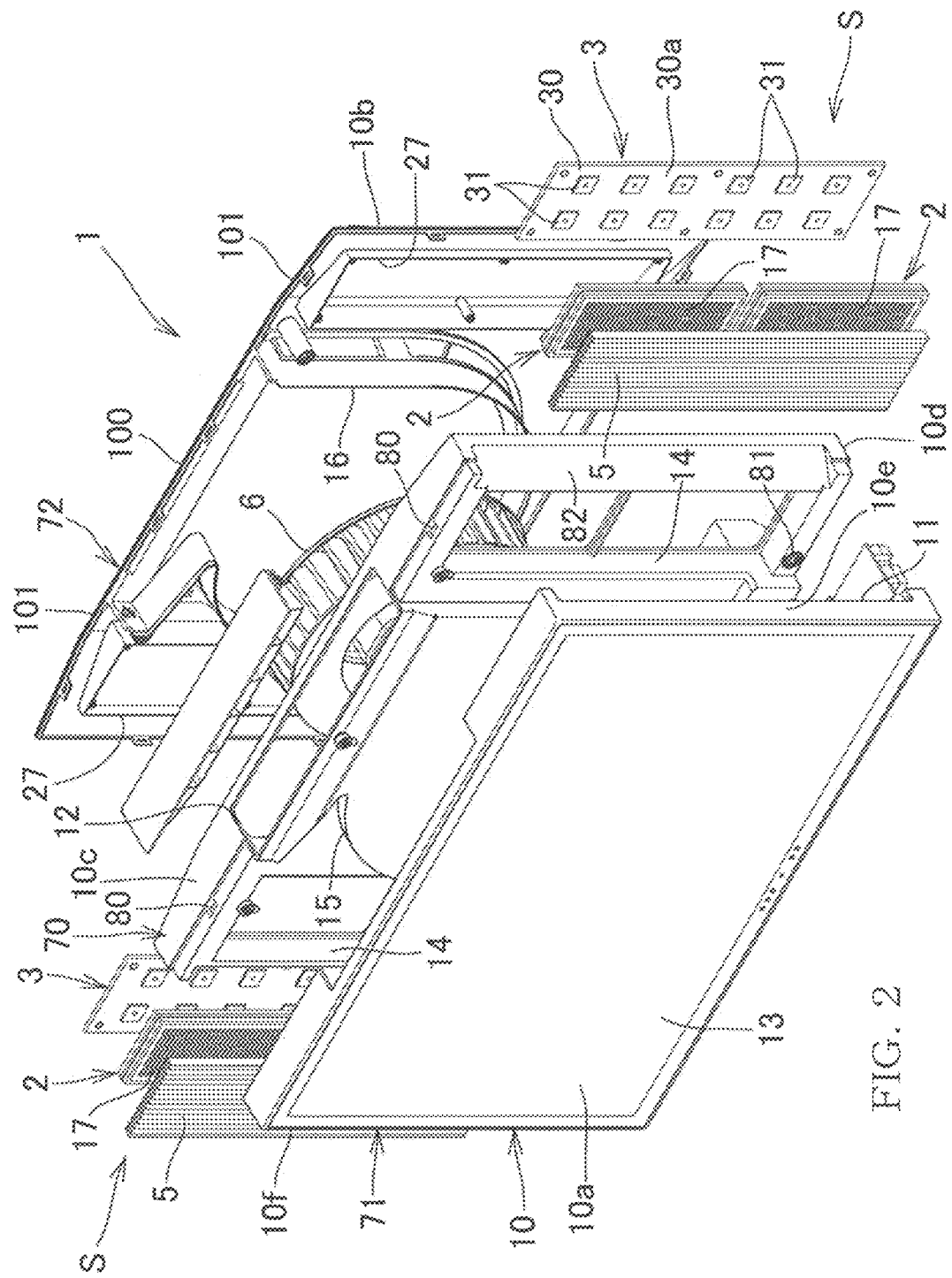
FIG. 2 is an exploded perspective view of the air cleaner of FIG. 1.
Figure 5A:
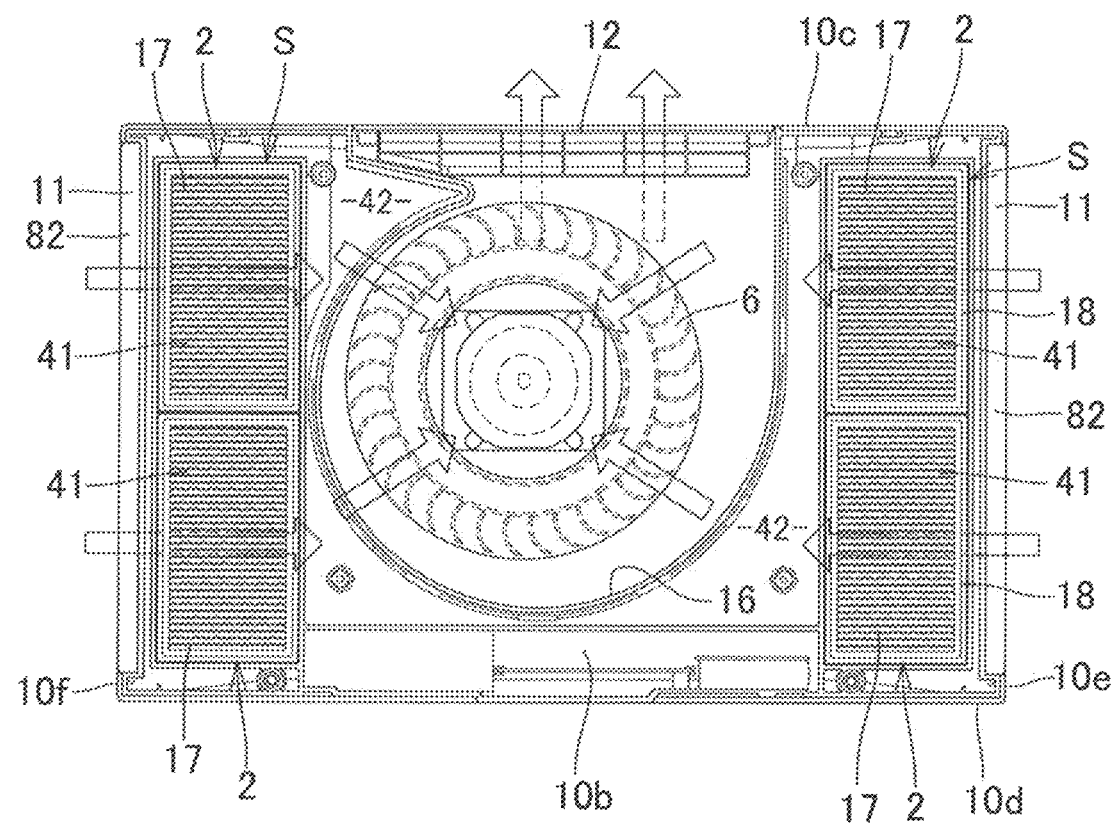
FIGS. 5A and 5B are explanatory diagrams showing flow of air.
Figure 5B:
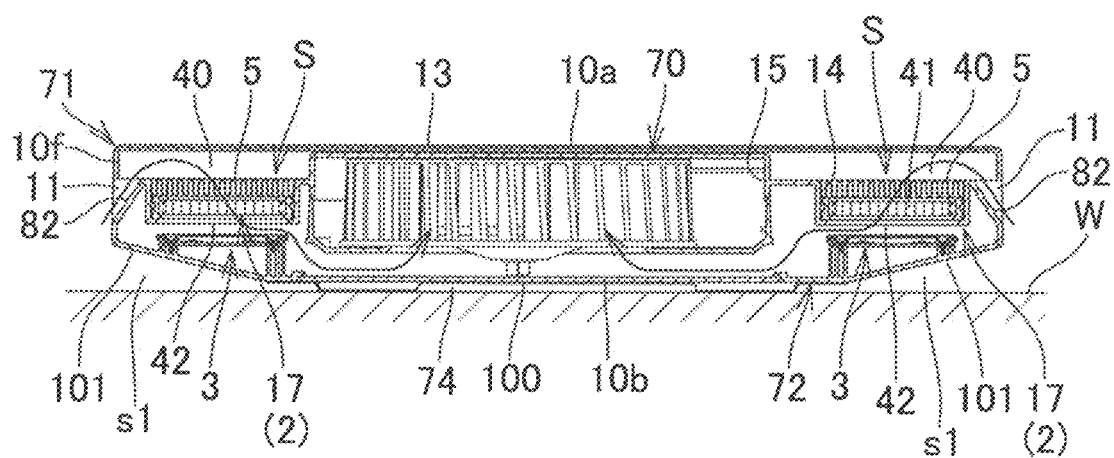
Figure 6:
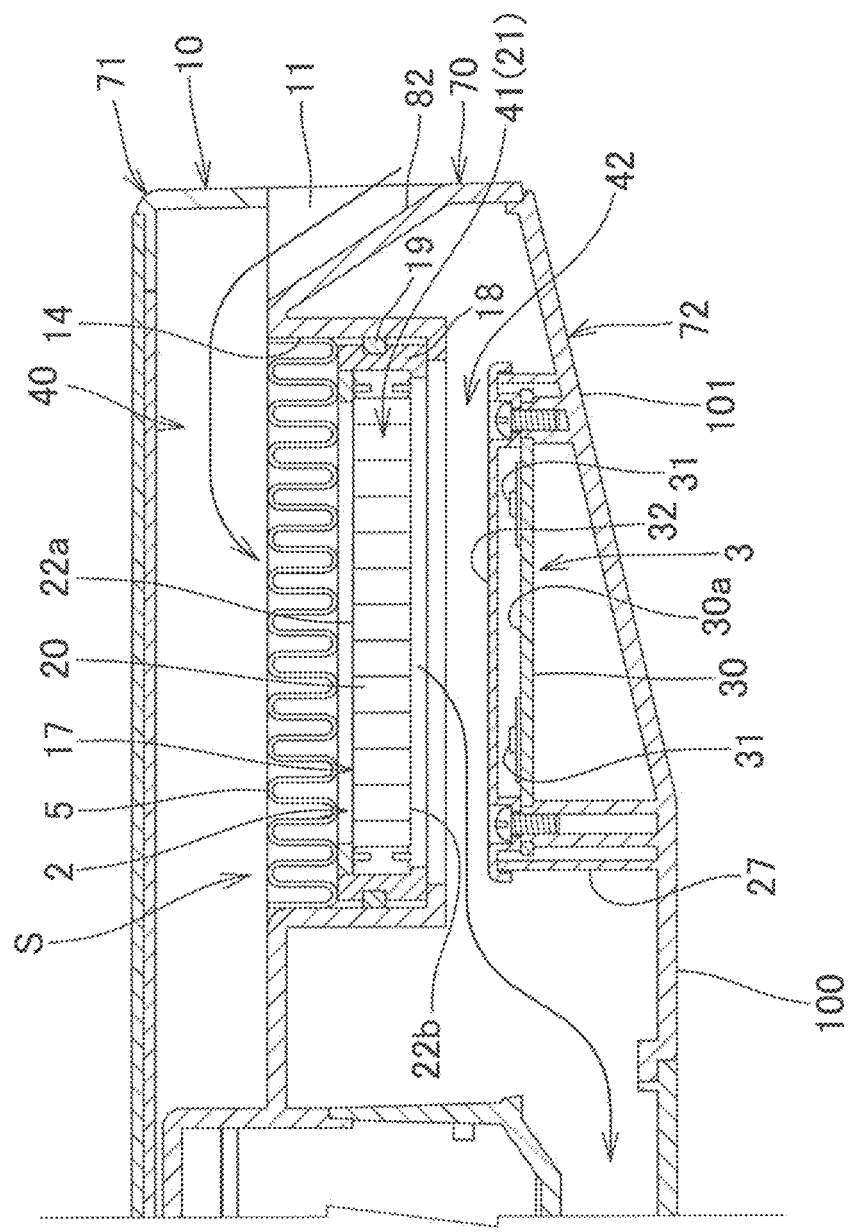
FIG. 6 is an enlarged explanatory diagram showing flow of air.

As shown in FIG. 5A, FIG. 5B and FIG. 6, in the housing 10, provided are an air supply path 40 that extends from the intake opening 11 to an air entrance of the photocatalytic filter 2, and an air discharge path 42 that extends from an air exit of the photocatalytic filter 2 to the discharge opening 12. A fan 6 that forces air to flow is provided in a middle of the air supply path 40 or the air discharge path 42. As shown in FIG. 2, the housing 10 includes: a front cover part 71 that is a constituent of the front wall 10a and has a display unit 13; a base body part 70 that has frame parts 14 to which photocatalytic filters 2 and a dust collection filter 5 are attached, and which are provided on the left and right sides, and on a rear surface side of which the fan 6 is attached; and a rear cover part 72 that is a constituent of the rear wall 10b and has fixing parts (frame parts 27) for fixing the respective UV irradiation units 3, which are provided at positions corresponding to the respective frame parts 14 on a front surface side, i.e., an inner surface side, of the rear cover part 72. In FIG. 2, a cover plate 32 that is a constituent of the UV irradiation unit 3 is not shown.

Figure 4:
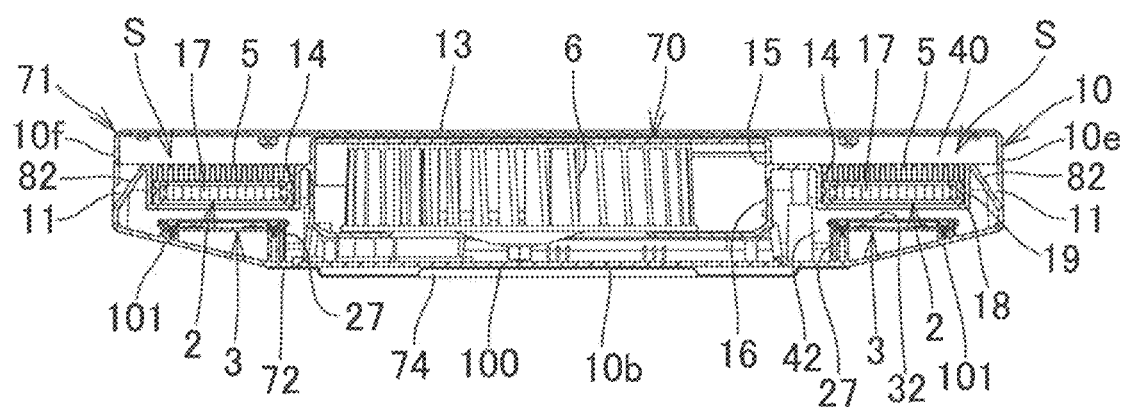
FIG. 4 is a horizontal cross-sectional view of the air cleaner of FIG. 1.

The air cleaner 1 of this example is configured as a wall-mounted type one that has the display unit 13 on a front surface thereof. As shown in FIG. 4, a wall-mount member 74 is provided on an outer surface of the rear wall 10b (the rear cover part 72). The rear wall 10b (the rear cover part 72) has a shape such that opposite side portions 101 thereof bend forward from a middle portion 100 thereof, i.e., the opposite side portions 101 are sloped forward with respect to the middle portion 100. Such a shape allows the air cleaner 1 to appear to be thin, in terms of external appearance. In addition, as shown in FIG. 5B, such a shape provides a structure that forms a large gap s1 between each side portion 101 and a wall surface W when the air cleaner 1 is mounted on a wall in use, so that the adhesion of dust in air to the wall surface can be prevented when air flows into the air cleaner 1 through the left and right intake openings 11 of the housing 10.

The display unit 13 can be configured to display pictures, photographs, liquid crystal screens, etc. A mirror can be attached to a front surface of the display unit 13 to provide a specular surface. The air cleaner 1 can be configured as a floor-standing type, or can be configured to additionally provide illumination when mounted on a ceiling. In the case where the air cleaner 1 is mounted on a ceiling, the display unit 13 is preferably provided with a light guide plate that is provided on the front surface thereof such that the light guide plate diffuses LED illumination light introduced thereinto from a lateral direction thereof, and thereby outputs uniform light to a front surface, and the air cleaner 1 is preferably mounted on a ceiling with the display unit 13 facing downward. As a result, the thin thickness can be maintained.

The lower wall 10d of the housing has an opening 73 through which outside air is taken into an odor sensor 7 that is provided on an inner surface side of the lower wall 10d. The operation of the fan 6, the amount of ultraviolet light emitted by the UV irradiation unit 3, etc., are control according to a signal from the sensor. A dust sensor is preferably provided instead of or in conjunction with the odor sensor.

Figure 3:
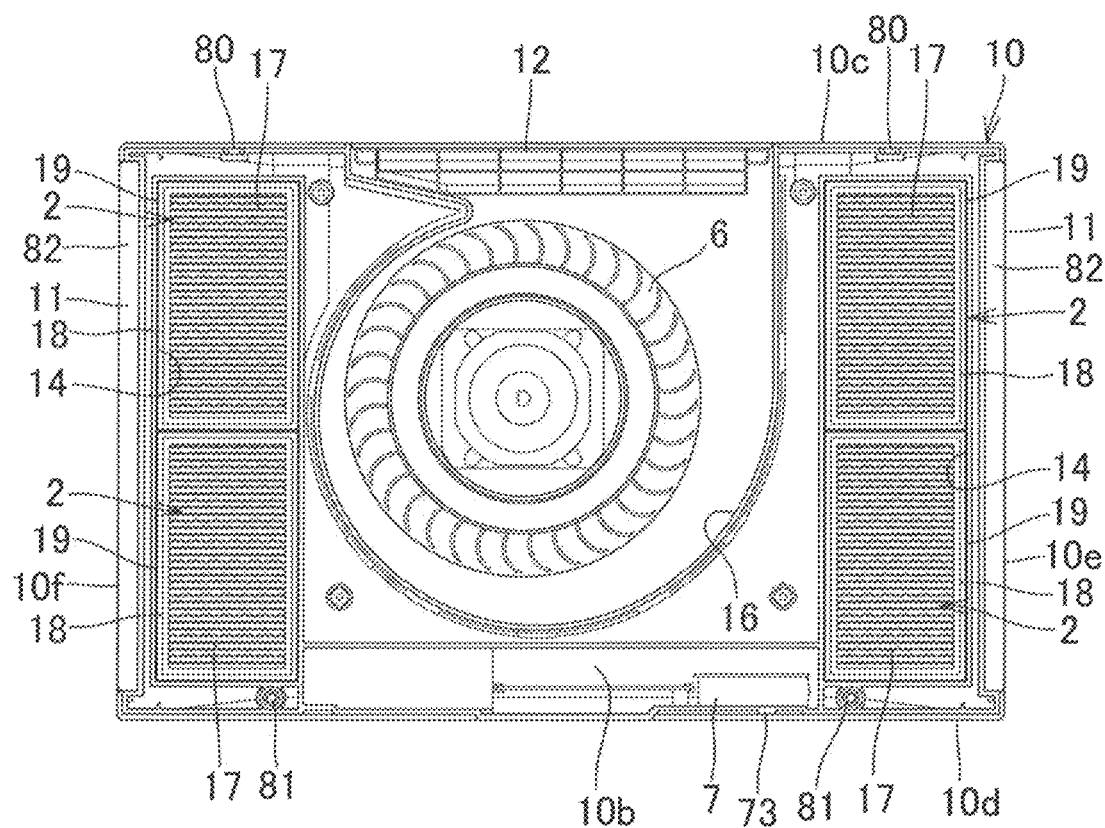
FIG. 3 is a vertical cross-sectional view of the air cleaner of FIG. 1.

As can be seen from FIGS. 2 and 3, the front cover part 71 is detachably attached to the base body part 70 by fastening hooks (not shown) provided on an inner surface of an upper portion of the front cover part 71 being engaged with respective fastening recessed portions 80 provided at corresponding positions on an upper surface of the base body part 70, and protrusions (not shown) provided on a rear surface of a lower portion of the front cover part 71 being fitted into respectively corresponding insertion holes 81 provided on a front surface of a lower portion of the base body part 70. When the front cover part 71 is removed from the base body part 70, the dust collection filters 5 and the photocatalytic filters 2 both of which are attached to the frame parts 14 appear and are made accessible, and therefore, can be easily maintained or replaced. FIG. 3 shows a state where the dust collection filters 5 are removed from the frame parts 14.

Partition walls 15, etc., constituting the air supply path 40 for supplying air from the left and right intake openings 11 to front surfaces of the photocatalytic filters 2 and the dust collection filters 5 both of which are attached to the frame parts 14, are suitably provided and protrude on a rear surface side, i.e., an inner surface side of the front cover part 71, and on a front surface side of the base body part 70. Partition walls 16, etc., constituting the air discharge path 42 for guiding, to the fan 6, air that has passed through the dust collection filters 5 and the photocatalytic filters 2 and then through gaps between the photocatalytic filters 2 and the UV irradiation units 3, and then has moved in a lateral direction, i.e., to a further inside area, and further guiding that air from the fan 6 to the discharge opening 12 above the fan 6, are provided and protrude on a rear surface side of the base body part 70 and on the front surface side of the rear cover part 72.

In this example, thus, air is introduced from left and right, is passed from a front surface side to a rear surface side of the photocatalytic filters 2, further flows in the gaps between the rear surface sides of the photocatalytic filters 2 and the UV irradiation units 3 toward a middle area, and is directed upward by the fan provided in a middle portion and then discharged out of the housing. The air cleaner 1 of the present invention is in no way limited to such an air flow form. Alternatively, an intake opening and a discharge opening can be provided in the upper, lower, left, and right peripheral walls in various arrangements, such as: an intake opening is provided in the lower wall in addition to the left and right walls; a discharge opening is provided in the lower wall instead of the upper wall; an intake opening is provided in the lower wall, and a discharge opening is provided in the left and right walls or the upper wall; and an intake opening and a discharge opening are provided in one and the other, respectively, of the left and right walls.

The intake opening 11 provided in each of the right wall 10e and the left wall 10f of the housing is provided with a guide wall 82 for guiding intake air to the front side of the frame part 14 to which the photocatalytic filters 2 are attached. The guide wall 82 extends from a rear portion of an opening edge of the intake opening 11 obliquely forward and toward the inside of the housing, and is continuously connected to a front end of the frame part 14. Air taken in through the intake opening 11 is guided through the air supply path 40 that is a space between the guide wall 82 and the front wall 10a, then through a flow path 41 extending from the front side of the frame part 14 through the dust collection filter 5 and the photocatalytic filters 2, and then through the air discharge path 42, to the fan 6.

The guide wall 82 thus configured is a constituent of the above-described air supply path 40 that guides air to the front side of the frame part 14 to which the photocatalytic filters 2 are attached, and also functions as a blocking wall that prevents external leakage, through the intake opening 11, of ultraviolet light emitted by the UV irradiation unit 3 that is positioned behind the frame part 14 in the housing 10.

In addition, although not shown, the housing 10 is preferably provided with: an operation button coupled to an internal control unit for controlling ultraviolet light emission of the UV irradiation unit 3, and operation of the fan 6, etc.; a light emission display unit that displays operation states (strong/weak) of the UV irradiation unit 3 and the fan 6, a state of air based on the odor sensor 7 or a dust sensor, etc., in the form of light emission, or an index, such as digits; a receiver unit for a remote controller signal; etc.

As shown in FIG. 7, FIG. 8A, FIG. 8B, FIG. 9A, FIG. 9B, FIG. 9C, FIG. 10A and FIG. 10B, the photocatalytic filter 2 includes a plurality of plate-shaped members 20, . . . on a front and a back surface of each of which a photocatalyst is carried, and which are arranged such that the front surface of one plate-shaped member 20 and the back surface of another plate-shaped member 20 adjacent thereto face each other with a gap 21 being interposed therebetween. The gaps 21 form the air flow path 41. In this example, the plate-shaped member 20 is a metal plate. The material for the plate-shaped member 20 may be selected as appropriate, such as a synthetic resin plate or cardboard.

More specifically, each plate-shaped member 20 has a pair of short sides facing each other and a pair of long sides facing each other. In this example, it is assumed that all the plate-shaped members 20 have the same shape and the same dimensions, and are evenly spaced with facing in the same direction and being parallel to each other. The outline of the entire photocatalytic filter 2 including the set of the plate-shaped members 20 is in the shape of a flat board having a uniform thickness.

The present invention is not limited to such a flat board-shape. The plate-shaped members 20 may have various shapes, such as a trapezoidal shape having a thickness that varies trapezoidally. In this example, the direction of the short side of each plate-shaped member 20 is the thickness direction of the flat board-shaped outline. Alternatively, all or a part of the short sides of the plate-shaped members 20 may be sloped. Alternatively, the plate-shaped members 20 may have different shapes from one onother. The plate-shaped members 20 may not be arranged parallel to each other, and may be arranged in a radial pattern, for example. The plate-shaped members 20 may be unevenly spaced.

As shown in FIG. 9A, FIG. 9B and FIG. 9C, in the photocatalytic filter 2, all the plate-shaped members 20 are linked and integrated together by linking members 23. These members constitute a unit arrangement, i.e., a metal filter base body 17. In this example, it is assumed that the linking member 23 is formed of a metal like the plate-shaped members 20. The present invention is not limited thereto. The linking member 23 may be formed of various materials, such as synthetic resin.

Specifically, as shown in FIG. 9B, a recessed notch 22c is formed in each of corner portions, i.e., four corners, of end surfaces 22a and 22b which are the long sides of each plate-shaped member 20. The recessed notches 22c provided in the corresponding corner portions of the plate-shaped members 20 are arranged in a straight line in a direction perpendicular to a direction in which the long side extends, i.e., in a direction in which the plate-shaped members 20 are arranged side by side. Four long linking members 23 are fitted into the four respective lines of recessed notches 22c.

Figure 11:
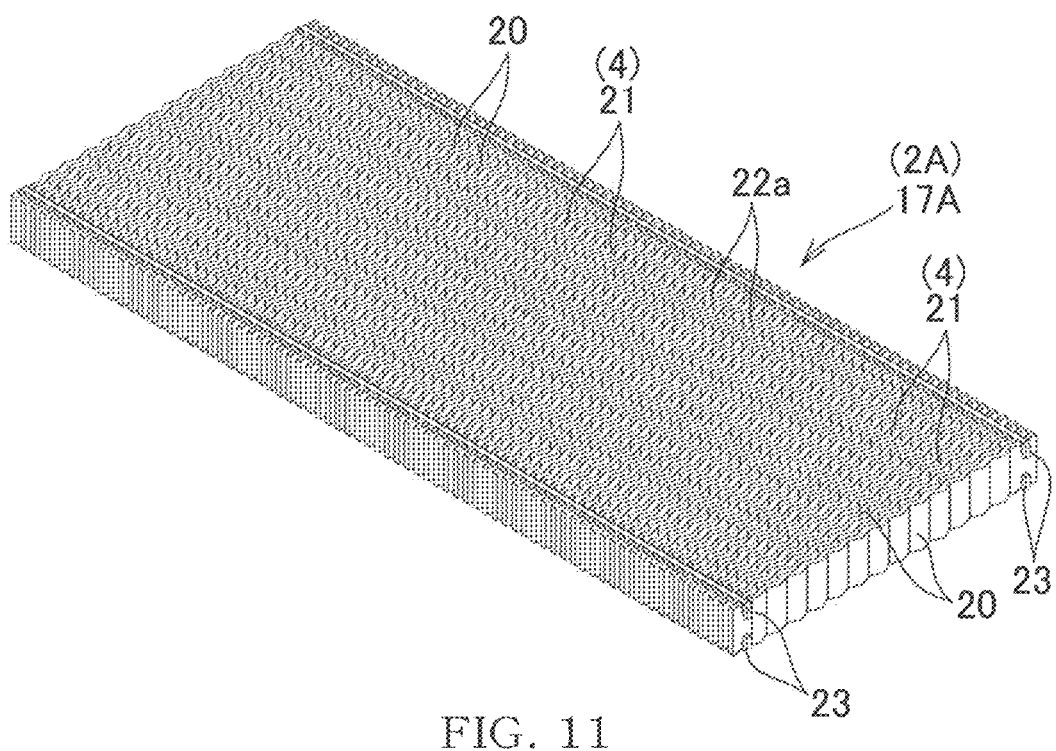
FIG. 11 is a perspective view showing another example of a metal filter base body.
Figure 12A:
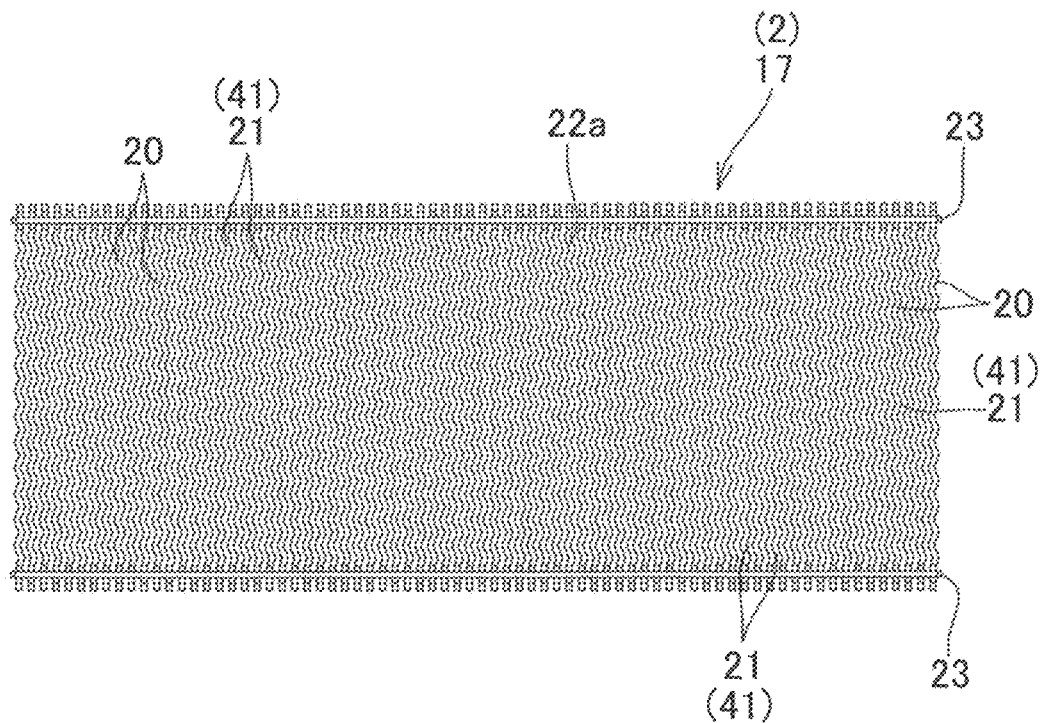
FIGS. 12A and 12B are a front view and a side view, respectively, showing the metal filter base body of FIG. 11.
Figure 12B:
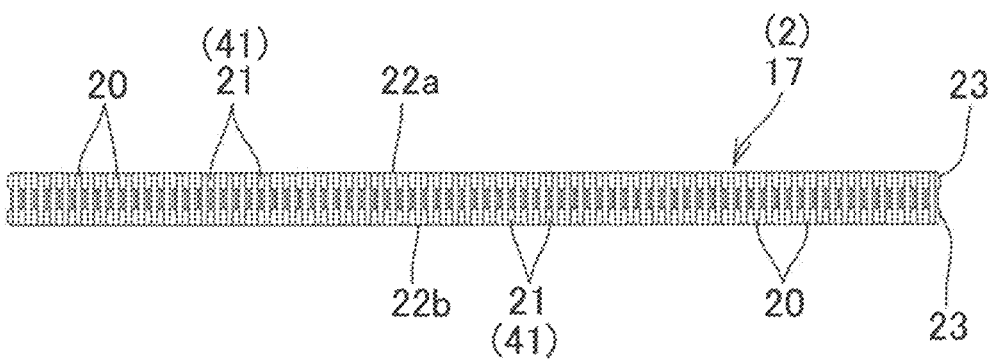

Each linking member 23 has recessed portions 23a that are interlocked with the respective corresponding recessed notches 22c of the plate-shaped members 20. The recessed portions 23a are successively provided in the longitudinal direction of each linking member 23 in a comb-like pattern. In this example, twice as many recessed portions 23a as necessary are formed so that a large number of plate-shaped members 20 can be accommodated. Therefore, the linking member 23 can be used as a common part. For example, as shown in FIGS. 11 and 12, if plate-shaped members 20 are attached to all the recessed portions 23a, the number of the plate-shaped members 20 doubles. Accordingly, the photocatalytic effect can be enhanced, though the gaps 21 are narrowed.

As shown in FIG. 9C, the recessed portions 23a are each crimped and fixed, with being interlocked with the respective corresponding recessed notches 22c of the plate-shaped members 20. In this example, each alternate one of the recessed portions 23a, the number of which is more than that of the recessed notches 22c, is interlocked with the corresponding recessed notch 22c, and fixed by being crimped. Thus, in the metal filter base body 17 of this example, the plate-shaped members 20 are integrated together into a unit using the four linking members 23. In addition to crimping, various joining means, such as brazing and an adhesive, can be used as appropriate.

Figure 7:
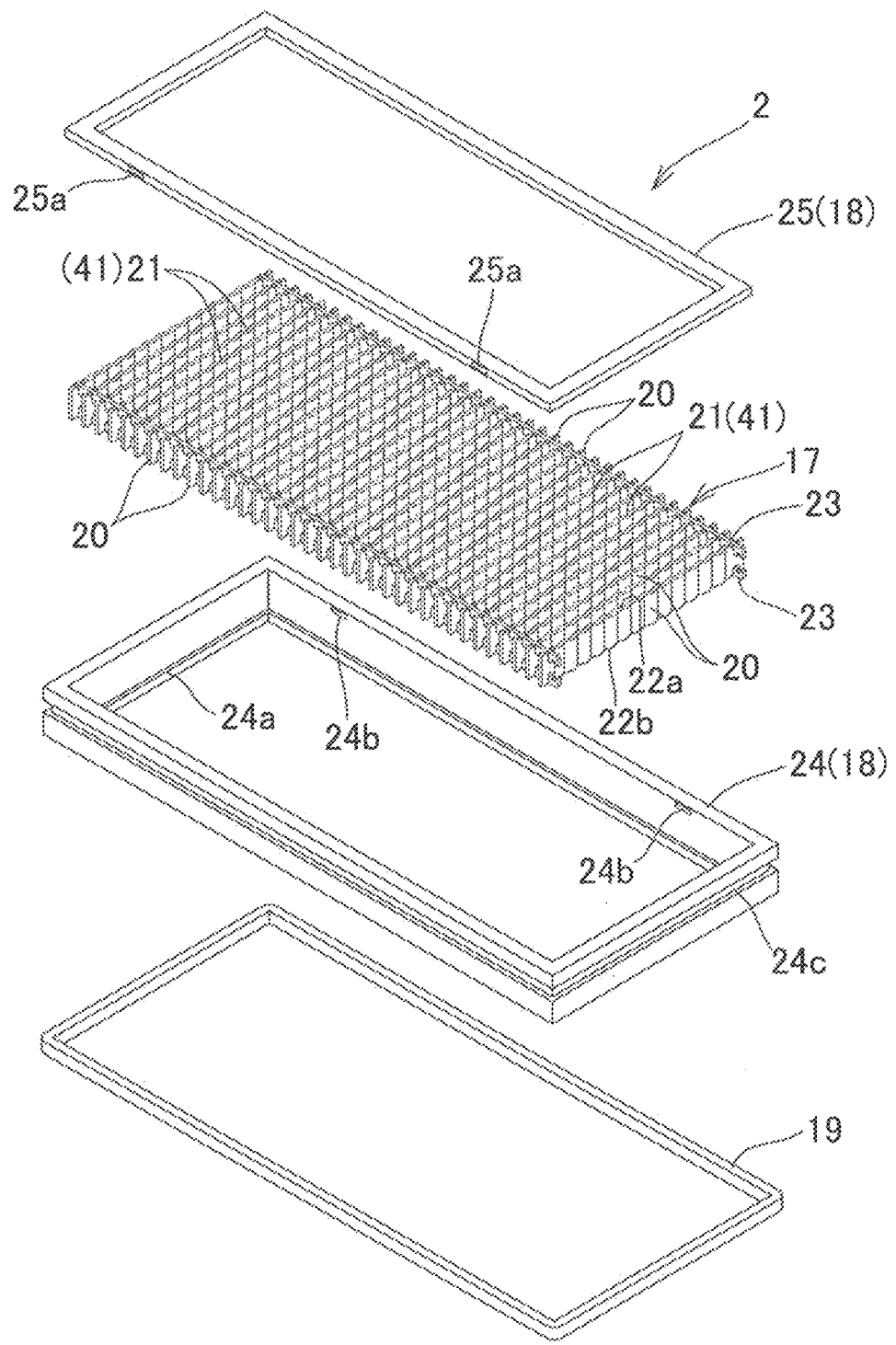
FIG. 7 is an exploded perspective view showing a photocatalytic filter.
Figure 8A:
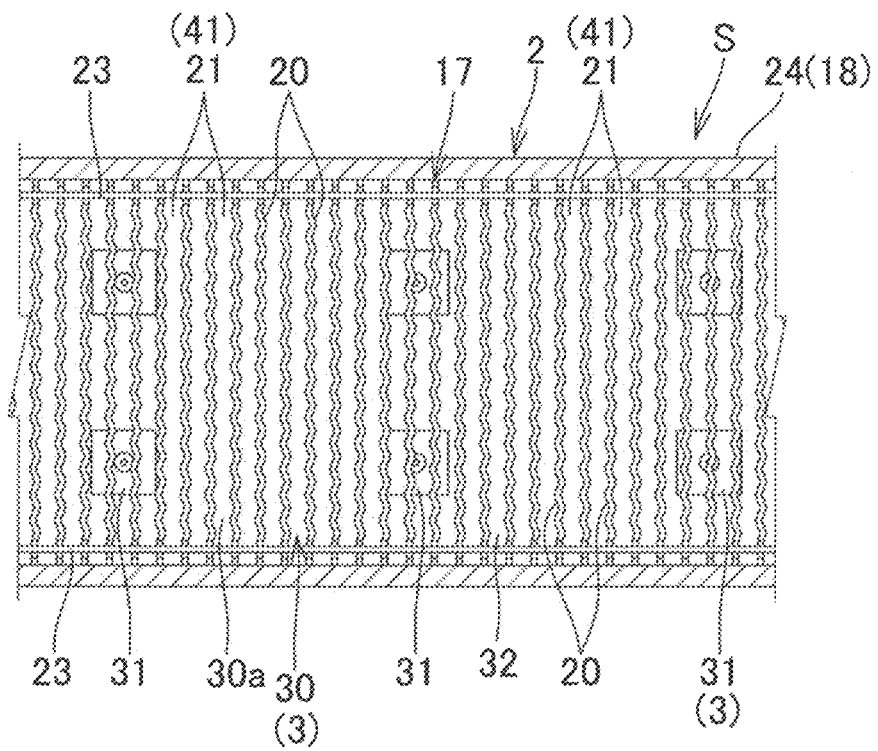
FIGS. 8A and 8B are a front view and a side view, respectively, showing an air cleaning structure including a photocatalytic filter.
Figure 8B:
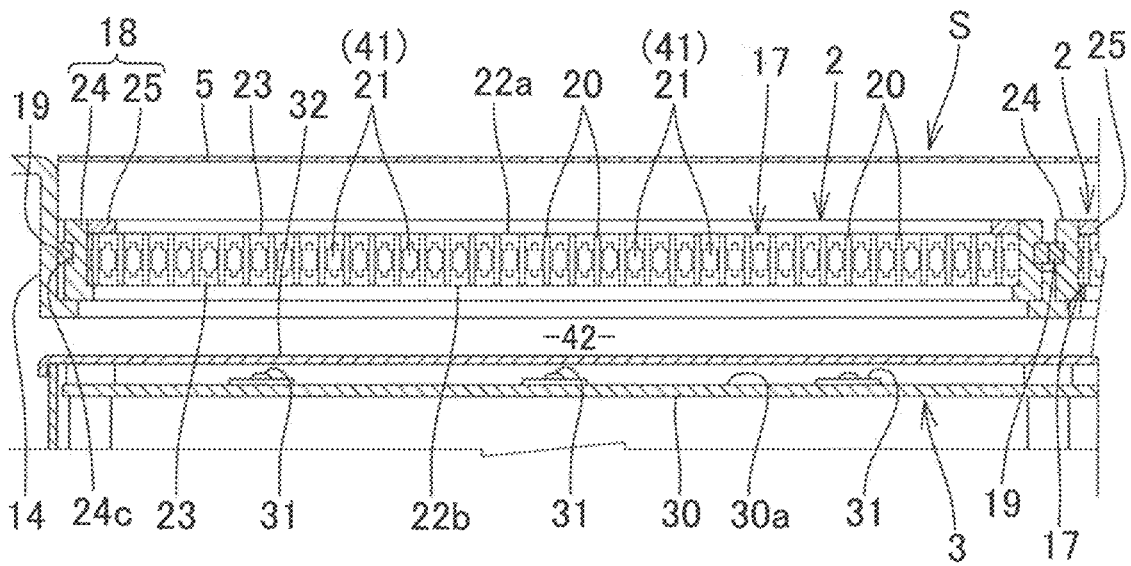
Figure 10A:
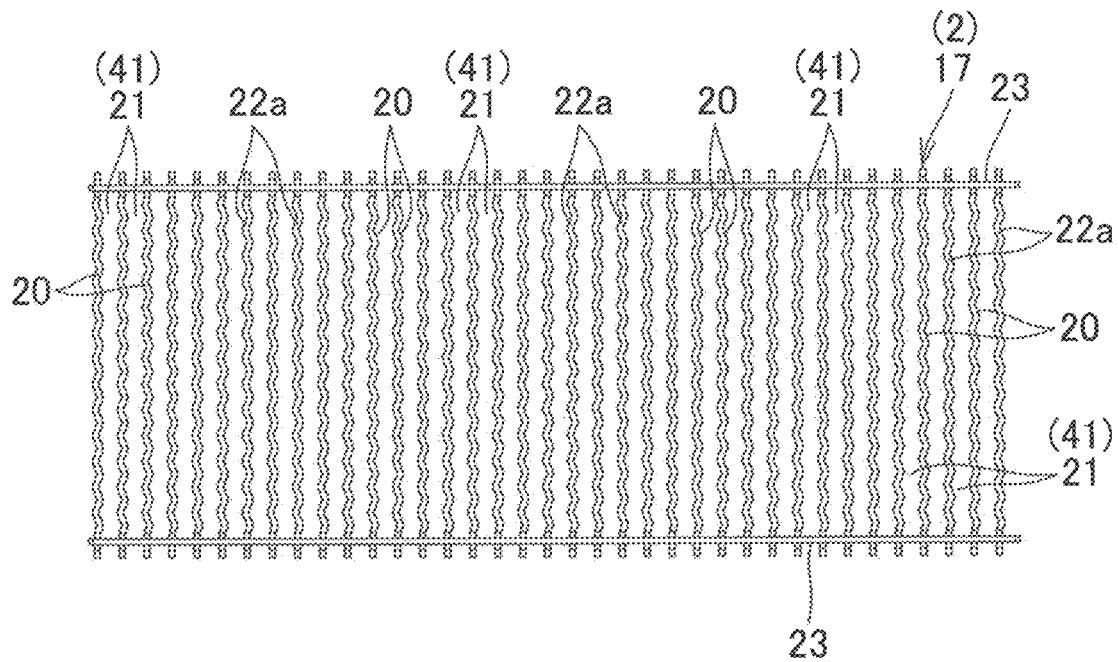
FIGS. 10A and 10B are a front view and a side view, respectively, showing the metal filter base body of FIG. 9.
Figure 10B:
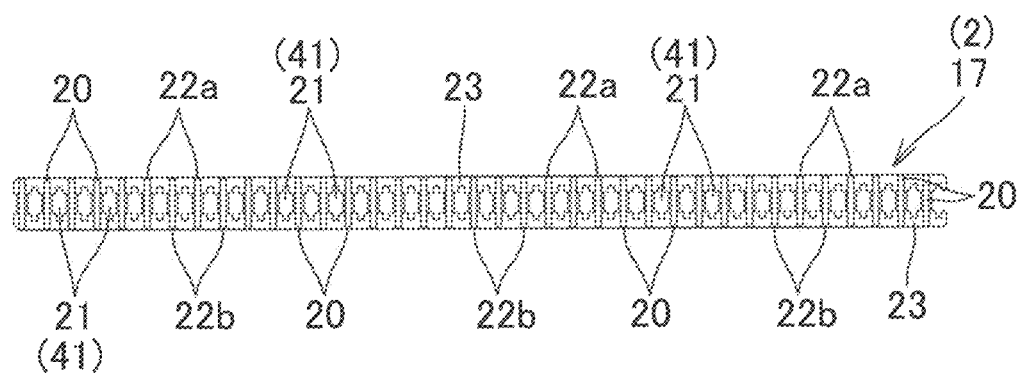

As shown in FIG. 7, FIG. 8A and FIG. 8B, the metal filter base body 17 is fitted into a tube-shaped frame 18 formed of synthetic resin to form the photocatalytic filter 2. The frame 18 includes: a frame body 24 having a hook piece 24a on which a peripheral end portion of one (in this example, a surface on the side where the end surface 22b of each plate-shaped member 20 is positioned) of the surfaces in the thickness direction of the flat board-shaped metal filter base body 17 is hooked, and which is provided and protrudes on an inner peripheral surface of the frame body 24; and an annular frame plate 25 on which a peripheral portion of the other surface (in this example, a surface on the side where the end surface 22a of each plate-shaped member 20 is positioned) of the metal filter base body 17 is hooked, with the metal filter base body 17 being hooked by the hook piece 24a on an inner peripheral side of the frame body 24 to be disposed inside thereof.

A plurality of protrusions 25a are provided on a peripheral end surface of the frame plate 25 at predetermined positions. Recessed notches 24b are provided on the inner peripheral surface of the frame body 24 at positions corresponding to the respective protrusions 25a. The frame plate 25 is removably attached to the frame body 24 by the protrusions 25a being engaged with the respective corresponding recessed notches 24b. When the metal filter base body 17 is maintained or replaced, the metal filter base body 17 can be easily removed or attached with the frame plate 25 being removed or attached.

In this example, the plate-shaped members 20, which are a metal plate, and the linking members 23, which are a linking element that is also formed of a metal, constitute the metal filter base body 17, which is attached to the frame 18 to construct the photocatalytic filter 2. Alternatively, for example, in the case where the plate-shaped member 20 is formed of a synthetic resin material, the frame may be used as a substitute for the linking members, and the plate-shaped members and the frame may be integrally formed by molding. This is also a preferable embodiment.

An annular sealing member 19 formed of a soft material is provided on an outer peripheral portion of the frame 18. Specifically, an annular recessed groove 24c is provided in the outer peripheral surface of the frame body 24, and the sealing member 19 is attached to the recessed groove 24c. The sealing member 19 is preferably formed of silicone rubber. By providing the sealing member 19, the photocatalytic filter 2 is tightly attached to the frame part 14 of the housing 10 and therefore is stably held. This tight attachment alone allows attachment and removal of the photocatalytic filter 2, resulting in good workability. In addition, the tight attachment increases hermeticity, so that air can reliably flow in the flow path 41 that is the gaps 21 of the photocatalytic filter 2. Furthermore, the tight attachment has the effect of preventing the occurrence of noise that is caused by the photocatalytic filter 2 shaking in the frame part 14.

The photocatalytic filter 2 is disposed in the housing 10 (the frame part 14) with the end surfaces 22a and 22b that are the pair of long sides facing each other of each plate-shaped member 20 being aligned in the fore-and-aft direction so that the end surface 22a is positioned on a side where air enters (hereinafter referred to as an "air entrance side") and the end surface 22b is positioned on a side where air exits (hereinafter referred to as an "air exit side"). In the air flow path 41 that is the gaps 21 between the plate-shaped members, air passes in a direction along the short sides of the plate-shaped members 20.

In this example, each plate-shaped member 20 is an undulating plate that undulates, i.e., alternately bends toward the front and the back, in a direction (long side direction) in which the end surfaces 22a and 22b extend. This increases the area of the front and back surfaces carrying the photocatalyst, so that the contact area between air passing in the gap 21 and the photocatalyst is increased, whereby the air cleaning effect is improved. Such an undulating plate-shape can be efficiently formed by pressing a flat plate-shaped member. In this example, the undulating sheet-shape has a gentle waveform. Alternatively, the angle of bending may be increased. Taking into account the irradiation with ultraviolet light, it is preferable that the plate-shaped member should extend straight in the short side direction. In addition, the plate-shaped member preferably has a hole or a cut-and-raised piece.

The photocatalyst is provided in the form of a titanium dioxide coating that is formed on and cover the front and back surfaces of the plate-shaped member 20. The titanium dioxide coating can be formed using a known method. The front and back surfaces of the plate-shaped member 20 are preferably roughened by sandblasting, etching, graining during pressing, chemical polishing, or a combination thereof, before the titanium dioxide coating is formed. When the photocatalyst is irradiated with ultraviolet light from the UV irradiation unit 3, OH radicals are generated, which decompose hazardous components and odor components in air.

As shown in FIG. 6, FIG. 8A and FIG. 8B, the UV irradiation unit 3 is positioned to face at least one of the end surfaces 22a and 22b that are the long sides of each plate-shaped member 20 (in this example, the end surface 22b that is positioned on the air exit side that is the rear surface side, of the photocatalytic filter 2), and is a predetermined distance away from the end surface 22b. The UV irradiation unit 3 is also positioned so as to irradiate the gaps 21 with ultraviolet light from that position. As a result, the above air discharge path 42, through which air exiting the flow path 41 of the photocatalytic filter 2 is discharged in a lateral direction substantially parallel to the end surfaces 22b, is formed between the UV irradiation unit 3 and the end surfaces 22b of the plate-shaped members 20 of the photocatalytic filter 2.

More specifically, the UV irradiation unit 3 includes: a substrate 30; an UV light source 31 that is attached to a surface 30a of the substrate 30 that faces the photocatalytic filters 2, and irradiates the gaps 21 (flow path 41) between the plate-shaped members with ultraviolet light; and a light transmissive cover plate 32 that is interposed between the substrate 30 and the photocatalytic filters 2, and covers the substrate 30 and the UV light source 31. The substrate 30 and the cover plate 32 are attached to a fixing part (frame part 27) in the housing 10, in a manner of facing the photocatalytic filters 2 with a gap that forms the air discharge path 42 being interposed therebetween, and extending across all the air exits of the photocatalytic filters 2.

In this example, the UV light source 31, which is a UV LED device, is mounted on the substrate 30 on which a circuit pattern is printed. The present invention is not limited thereto. The substrate 30 is preferably a glass epoxy substrate, which has excellent strength, thermal conductivity, resistance to heat, and electrical characteristics. A metal sheet of aluminum, etc., is preferably attached to at least a rear surface side of the substrate 30, to provide a heat dissipation effect.

As shown in FIG. 6, air that moves from the front surface side of the photocatalytic filter 2 through the gaps 21 (flow path 41) between the plate-shaped members to the rear surface side of the photocatalytic filter 2, is mainly discharged through the gap (the air discharge path 42) between the cover plate 32 of the UV irradiation unit 3 and the end surfaces 22b on the air exit side of the plate-shaped members 20, along a front surface of the cover plate 32, toward a side end of the cover plate 32 (toward the center of the housing). Part of the air is passed between a back surface of the cover plate 32 and the substrate 30. The cover plate 32 prevents accumulation of dust, etc., on the substrate 30 and the UV light source 31. Dust, etc., accumulated on the cover plate 32 can be removed by only cleaning the cover plate 32 when the photocatalytic filters 2 are maintained or replaced.

Heat occurring in the UV irradiation unit 3 due to heat generation from the UV light source 31 is efficiently removed by air flowing in the air discharge path 42. In particular, the UV LED device generates heat, which causes degradation of the device itself. In the present invention, air is discharged in a lateral direction in the gap between the photocatalytic filters 2 and the UV irradiation unit 3, and therefore, heat can be efficiently discharged as described above, whereby the durability of the UV LED device can be increased.

Thus, in this example, the UV irradiation unit 3 is positioned to face the air exit side (in this example, the rear surface side) of the photocatalytic filters 2. Alternatively, the UV irradiation unit 3 may be positioned to face the end surfaces 22a on the air entrance side and to be a predetermined distance away from the end surfaces 22a so that the UV irradiation unit 3 emits ultraviolet light toward the gaps 21. Thus, an air supply path 40 may be formed, through which air is taken into a space between the UV irradiation unit 3 and the end surfaces 22a of the plate-shaped members 20 of the photocatalytic filters 2, from a lateral direction substantially parallel to the end surfaces 22a, and the air is supplied to the flow path 41 of the photocatalytic filters 2. Alternatively, a UV irradiation unit may be provided on both the air entrance side and air exit side of the photocatalytic filters 2 in a similar manner, and a similar air discharge path 42 and air supply path 40 may be formed.

In the air cleaner 1 of the present invention, the plate-shaped members 20, on the front and back surfaces of which a photocatalyst is carrired, are arranged such that the front surface of one plate-shaped member and the back surface of another one adjacent thereto face each other with a gap being interposed therebetween, to form the photocatalytic filter 2, in which the gaps 21 form the air flow path 41. In addition, the UV irradiation unit 3 is positioned away from the end surfaces 22a/22b on the air entrance side or air exit side of the plate-shaped members 20 of the photocatalytic filters 2. In addition, between the UV irradiation unit 3 and the end surfaces 22a/22b of the plate-shaped members, the air cleaning structure S is provided which forms the air supply path 40 for taking in air from a lateral direction substantially parallel to the end surfaces, or the air discharge path 42 for discharging air in a lateral direction substantially parallel to the end surfaces.

The air cleaning structure S thus configured, which is different from the conventional structure in which air is supplied or discharged through a gap between each UV lamp, has significantly improved flexibility in the design of the UV irradiation unit 3. Therefore, the UV irradiation unit 3 is easily designed such that ultraviolet light from the UV irradiation unit 3 also efficiently reaches deep inside each gap 21. In a preferable example, a scattering plate or a prism may be provided between the photocatalytic filters 2 and the UV irradiation unit 3 in order to more efficiently irradiate the inside of the gaps 21.

In addition, even in the case where air is taken into or discharged from a space between the UV irradiation unit and the end surfaces of the plate-shaped members, from or to a lateral direction, air can be passed through the gaps 21 (flow path 41) between the plate-shaped members without becoming stagnant. During the passage, the air can be efficiently cleaned by the photocatalyst provided on the front and back surfaces of the plate-shaped members. Furthermore, air is supplied to or discharged from the photocatalytic filters, from or to a lateral direction of the gap between the photocatalytic filters 2 and the UV irradiation unit 3. Therefore, unlike the conventional art, it is not necessary to provide an air supply path or an air discharge path on the opposite side of the UV irradiation unit, and therefore, the thickness of the entire air cleaner can be reduced, resulting in a reduction in thickness or size of the air cleaner.

As shown in FIG. 6, the air supply path 40 and the air discharge path 42 are configured such that air is supplied to and discharged from the photocatalytic filter 2, from and to a lateral direction substantially parallel to the end surfaces 22a/22b of the plate-shaped members 20 and along the direction in which the end surfaces extend. As a result, air can be uniformly and efficiently supplied to and discharged from all the gaps 21 between the plate-shaped members. In this example, air is taken in from a lateral direction, the air supply path 40 extends along the lateral direction, and the air discharge path 42 extends from the photocatalytic filter 2 toward a center where the fan 6 is provided. Therefore, the photocatalytic filter 2 may be set such that the direction in which the end surfaces 22a and 22b of each plate-shaped member extend is the lateral direction.

The dust collection filter 5 having a white or whitish color is positioned on the air entrance side of the photocatalytic filters 2 to occlude the entrances of the photocatalytic filters 2 so that dust, etc., in air is not accumulated in the gaps 21 between the plate-shaped members of the photocatalytic filters 2. The dust collection filter 5, which is corrugated, is fitted into the frame part 14 that holds the photocatalytic filters 2, and thereby attached to the frame part 14. The dust collection filter 5 is sized so as to cover the entire entrance of the two photocatalytic filters 2 arranged side by side. Alternatively, two dust collection filters 5 may be provided, one for each photocatalytic filter 2.

The dust collection filter 5 is preferably a high efficiency particulate air (HEPA) filter formed of a filtration material, such as glass fibers or synthetic fibers, or alternatively, may be other dust collection filters. Ultraviolet light emitted from the UV irradiation unit 3 provided on the air exit side (rear surface side) of the photocatalytic filters 2 to the gaps 21 between the plate-shaped members is reflected by the dust collection filter 5 disposed on the air entrance side (front surface side) of the photocatalytic filters 2, and therefore, the photocatalyst in the gaps 21 is more efficiently irradiated with the ultraviolet light. Concerning the color of the dust collection filter 5, a filter base preferably has a white or whitish color, and a film that transmits substantially no ultraviolet light is preferably formed on a front surface side of the filter base, which is opposite to a rear surface side facing the UV irradiation unit 3. If at least the rear surface side has a white or whitish color, ultraviolet light is reflected, so that the photocatalyst in the gaps 21 of the photocatalytic filters 2 is efficiently irradiated with ultraviolet light. Therefore, the filter base may have a non-white or non-whitish color, and a white or whitish film may be formed on only the rear surface side or all surfaces of the filter base.

Figure 13:
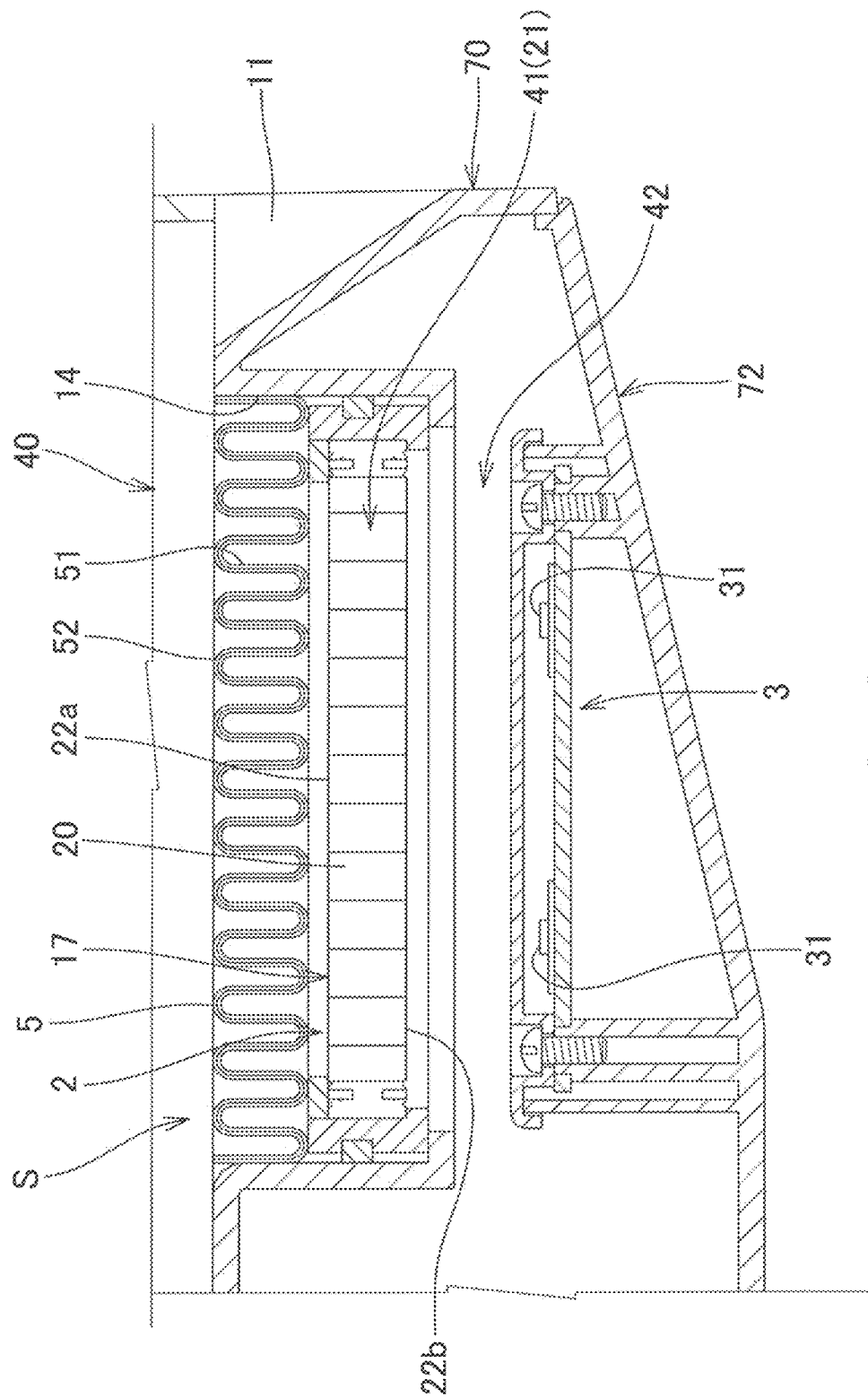
FIG. 13 is an explanatory diagram of a main portion of a variation of a dust collection filter.

FIG. 13 shows a variation of the dust collection filter 5 that has a two-layer structure including a first filter layer 51 disposed on the rear surface side that faces the photocatalytic filter 2, and a second filter layer 52 disposed on the front surface side. The first filter layer 51 includes a white or whitish base, on at least a rear surface side of which a photocatalyst is carried by rubbing, etc. The second filter layer 52 is formed of electric nonwoven fabric, and preferably has a white or whitish color as with the first filter layer 51, or alternatively may have other colors.

First of all, the dust collection filter 5, which has such a two-layer structure, efficiently captures dust, etc., in air using the second filter layer 52. In addition, ultraviolet light emitted from the UV irradiation unit 3, which is disposed on the air exit side (rear surface side) of the photocatalytic filters 2, to the gaps 21 between the plate-shaped members, is reflected by the first filter layer 51 and then returned to the gaps 21, so that the photocatalyst inside the gaps 21 can be more efficiently irradiated with ultraviolet light. In addition, the first filter layer 51 itself also carries a photocatalyst, and therefore, dust, etc., captured by the first filter layer 51, and air passing through the first filter layer 51, can be cleaned by the photocatalytic effect. The photocatalytic effect of the first filter layer 51 can also decompose viruses, etc., that are captured by the second filter layer 52 and then move to the first filter layer 51.

The first filter layer 51 and the second filter layer 52 are both preferably formed of a filtration material layer of glass fibers, synthetic fibers, etc. The two-layer structure of this example may be in an integrated form. Alternatively, the first filter layer 51 and the second filter layer 52 may be two separate filters that are only put on top of each other, or may be joined together.

Figure 14:
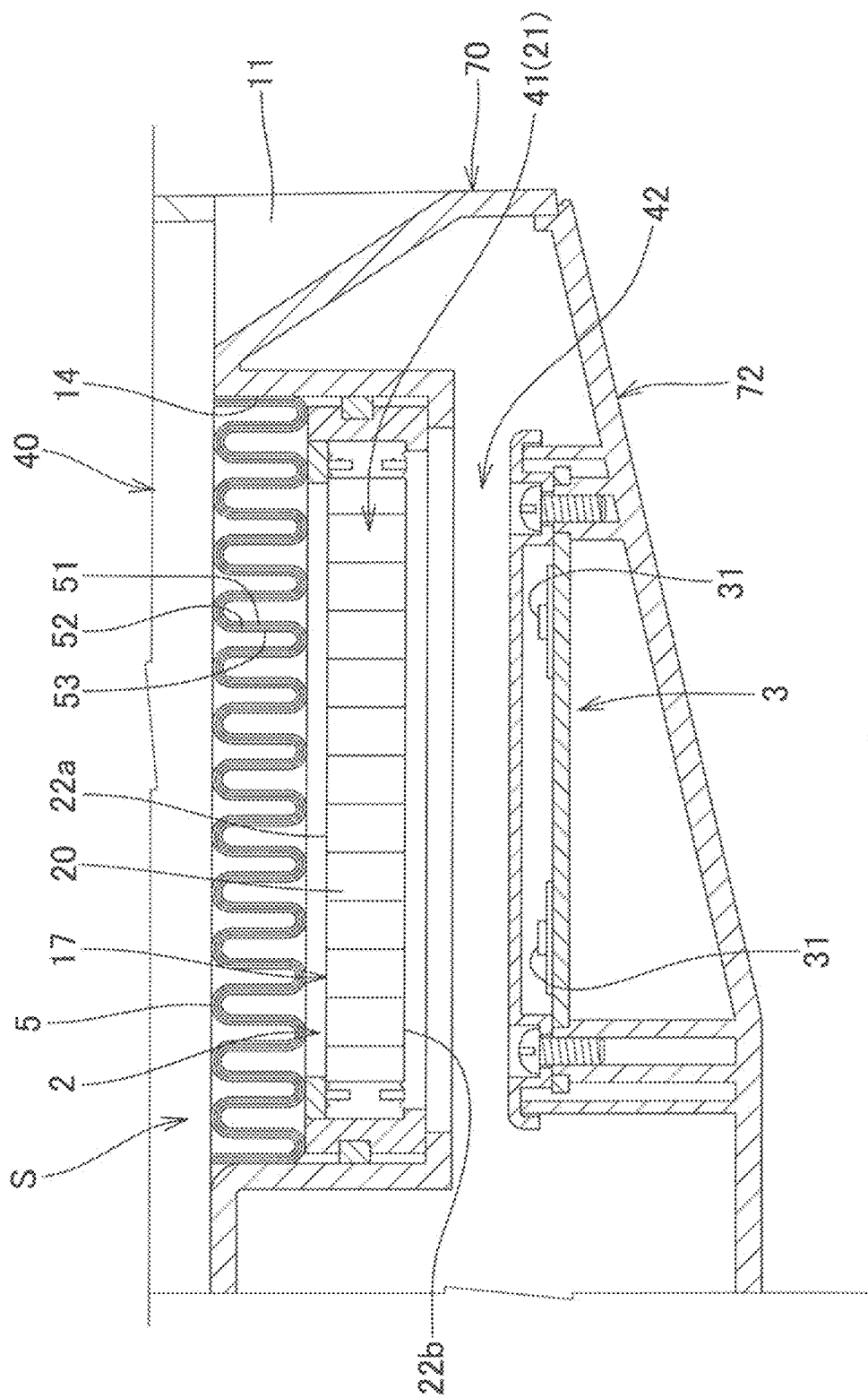
FIG. 14 is an explanatory diagram of a main portion ofanother variation of a dust collection filter.

FIG. 14 shows a variation of the dust collection filter 5 in which, in addition to the first filter layer 51 and the second filter layer 52 shown in FIG. 13, a third filter layer 53 is provided on a front surface side of the second filter layer 52. The third filter layer 53 is formed of a layer on which activated charcoal particles are carried by rubbing, etc., and therefore, has a dark color.

The third filter layer 53 thus configured efficiently captures dust and odor components in air. In addition, even when ultraviolet light that leaks from the gaps 21 of the photocatalytic filter 2 to the front surface side passes through the first filter layer 51 and the second filter layer 52, the third filter layer 53 can adsorb that ultraviolet light, so that ultraviolet light does not leak to the front surface of the dust collection filter 5. Therefore, leakage from the housing can be more reliably prevented. In addition, as with the example of FIG. 13, viruses, etc., that are captured by the third filter layer 53 and then move to the second filter layer 52 and then to the first filter layer 51, can be decomposed by the photocatalytic effect of the first filter layer 51.

Next, a second embodiment of the present invention will be described with reference to FIG. 15, FIG. 16, FIG. 17, FIG. 18, FIG. 19, FIG. 20, FIG. 21, FIG. 22, FIG. 23, FIG. 24 and FIG. 25.

Figure 16:
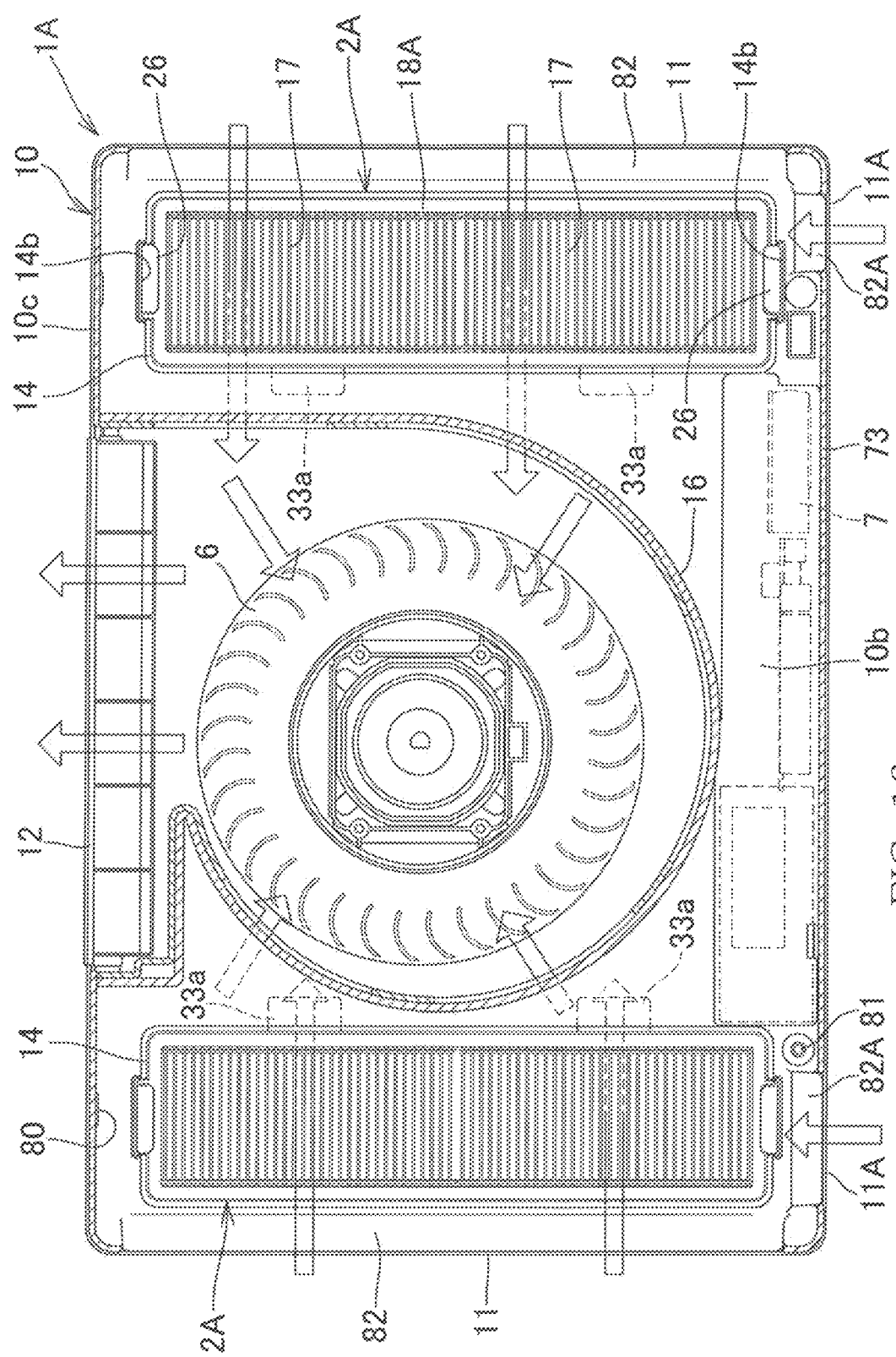
FIG. 16 is a vertical cross-sectional view showing the air cleaner of FIG. 15, where arrows show flow of air.
Figure 17:
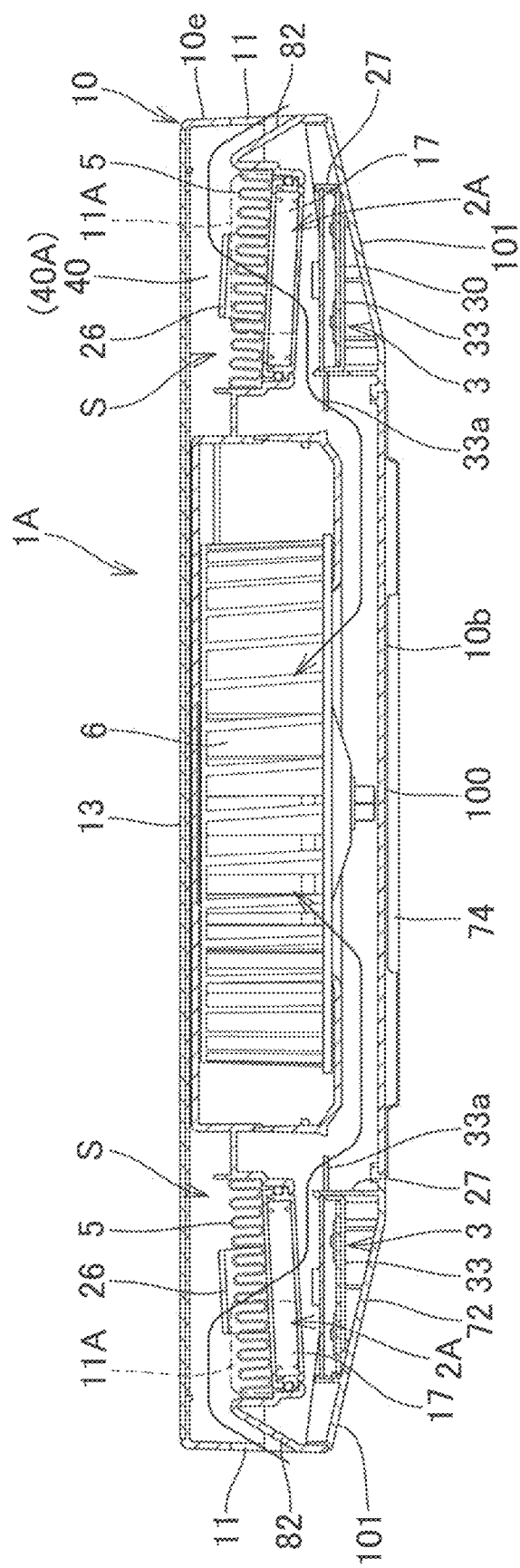
FIG. 17 is a horizontal cross-sectional view showing the air cleaner of FIG. 15.
Figure 18:
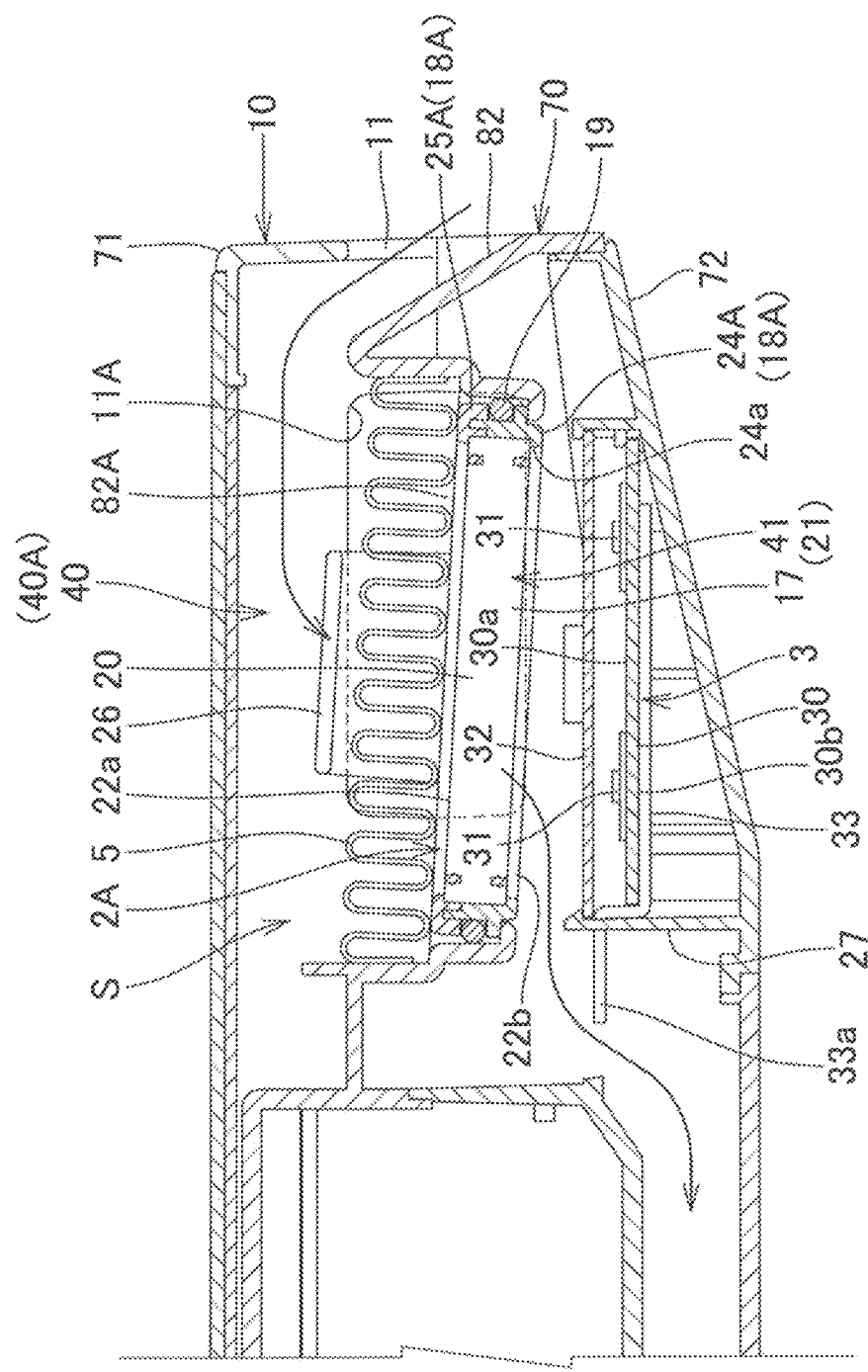
FIG. 18 is an exploded explanatory diagram showing flow of air.
Figure 19:
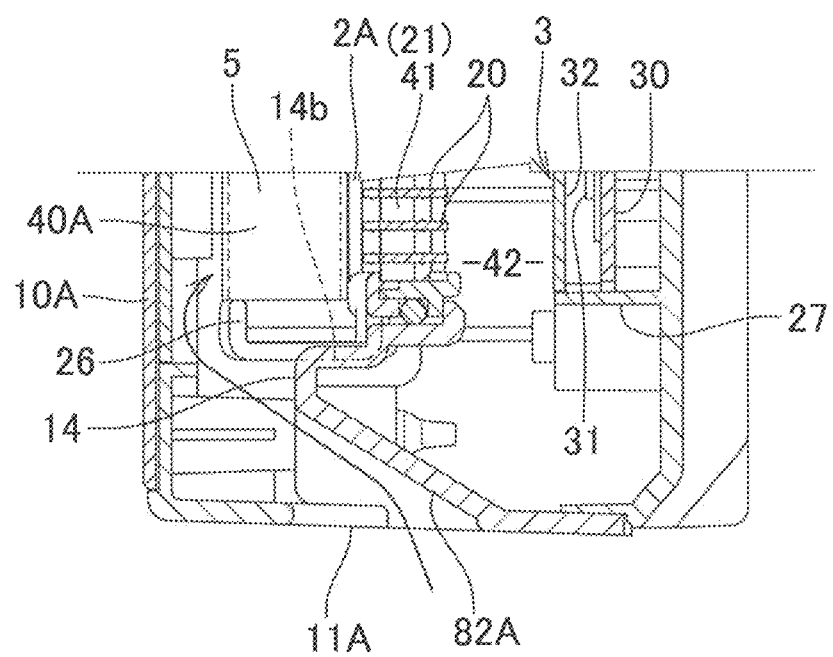
FIG. 19 is an enlarged explanatory diagram showing flow of air.

As shown in FIG. 15, FIG. 16, FIG. 17, FIG. 18 and FIG. 19, an air cleaner 1A of this embodiment is provided with, in addition to the intake openings 11 in the left and right walls of the housing 10, intake openings 11A through which air is taken into the housing 10, in side portions of the lower wall 10d. As a result, as shown in FIGS. 18 and 19, in the housing 10, an air supply path 40A extending from the intake opening 11A to the air entrance of the photocatalytic filter 2 is formed in addition to the air supply path 40 extending from the intake opening 11 to the air entrance of the photocatalytic filter 2.

The intake openings 11A are provided in the respective side portions of the lower wall 10d corresponding to the opposite side portions 101 of the rear wall 10b (the rear cover part 72). Therefore, a structure is provided that can prevent adhesion to the wall surface of dust in air flowing in through the intake openings 11A, as in the case of the intake openings 11. By thus providing the intake openings 11A, the air intake efficiency of the air cleaner can be improved, and air below the air cleaner 1A can also be taken in and is allowed to flow without becoming stagnant, so that the odor sensor 7 or a dust sensor provided on the inner surface side of the lower wall 10d of the housing can also have good sensitivity.

As in the first embodiment, partition walls 15, etc., are provided and protrude, as appropriate, on the rear surface side, i.e., the inner surface side, of the front cover part 71 and on the front surface side of the base body part 70. The partition walls 15, etc., form the air supply paths 40 and 40A through which air is supplied from the left and right intake openings 11 to the front surfaces of the photocatalytic filters 2 and the dust collection filters 5 attached to the frame parts 14.

In this example, air is thus introduced from left, right, and below, is passed from the front surface side to the rear surface side of the photocatalytic filters 2, further flows in the gaps between the rear surfaces of the photocatalytic filters 2 and the UV irradiation units 3 toward a middle area, and is directed upward by the fan provided in a middle portion and discharged out of the housing. Various other arrangements can be provided. For example, an intake opening may be provided only in the lower wall, and a discharge opening may be provided in the left and right walls or the upper wall. Alternatively, an intake opening and a discharge opening may both be provided in the lower wall.

As shown in FIG. 19, as with the intake opening 11, the intake opening 11A is provided with a guide wall 82A for guiding intake air to the front side of the frame part 14 to which the photocatalytic filters 2 are attached. The guide wall 82A extends from a rear portion of an opening edge portion of the intake opening 11A obliquely forward and toward the inside of the housing, and is continuously connected to a front end of the frame part 14. Air taken in through the intake opening 11A is guided through the air supply path 40A that is a space between the guide wall 82A and the front wall 10a, then through the flow path 41 extending from the front side of the frame part 14 through the dust collection filter 5 and the photocatalytic filters 2, and then through the air discharge path 42, to the fan. In addition, as with the guide wall 82, the guide wall 82A also functions as a blocking wall for preventing external leakage of ultraviolet light emitted by the UV irradiation unit 3 through the intake opening 11A.

In addition, in this example, as can also be seen from FIGS. 17 and 18, the frame part 14 to which the photocatalytic filters 2A and the dust collection filter 5 are attached is in an oblique position such that a portion thereof closer to the center is closer to the front. As a result, the gap between the photocatalytic filter 2A and the UV irradiation unit 3 becomes wider toward the center portion, and therefore, a pressure loss of air is reduced, resulting in an increase in flow efficiency. The frame part for attachment of the UV irradiation unit 3 may be in an oblique position such that a portion thereof closer to the center is closer to the rear, which provides a similar effect. These arrangements may be combined.

In this example, a single photocatalytic filter 2 is provided on each of the left and right sides, i.e., a total of two photocatalytic filters 2 are provided. As in the first embodiment, each photocatalytic filter 2A includes a plurality of plate-shaped members 20, . . . , on a front and a back surface of which a photocatalyst is carried, and which are arranged such that the front surface of one plate-shaped member 20 and the back surface of another plate-shaped member 20 adjacent thereto face each other with a gap 21 being interposed therebetween. The gaps 21 form the air flow path 41.

Figure 20:
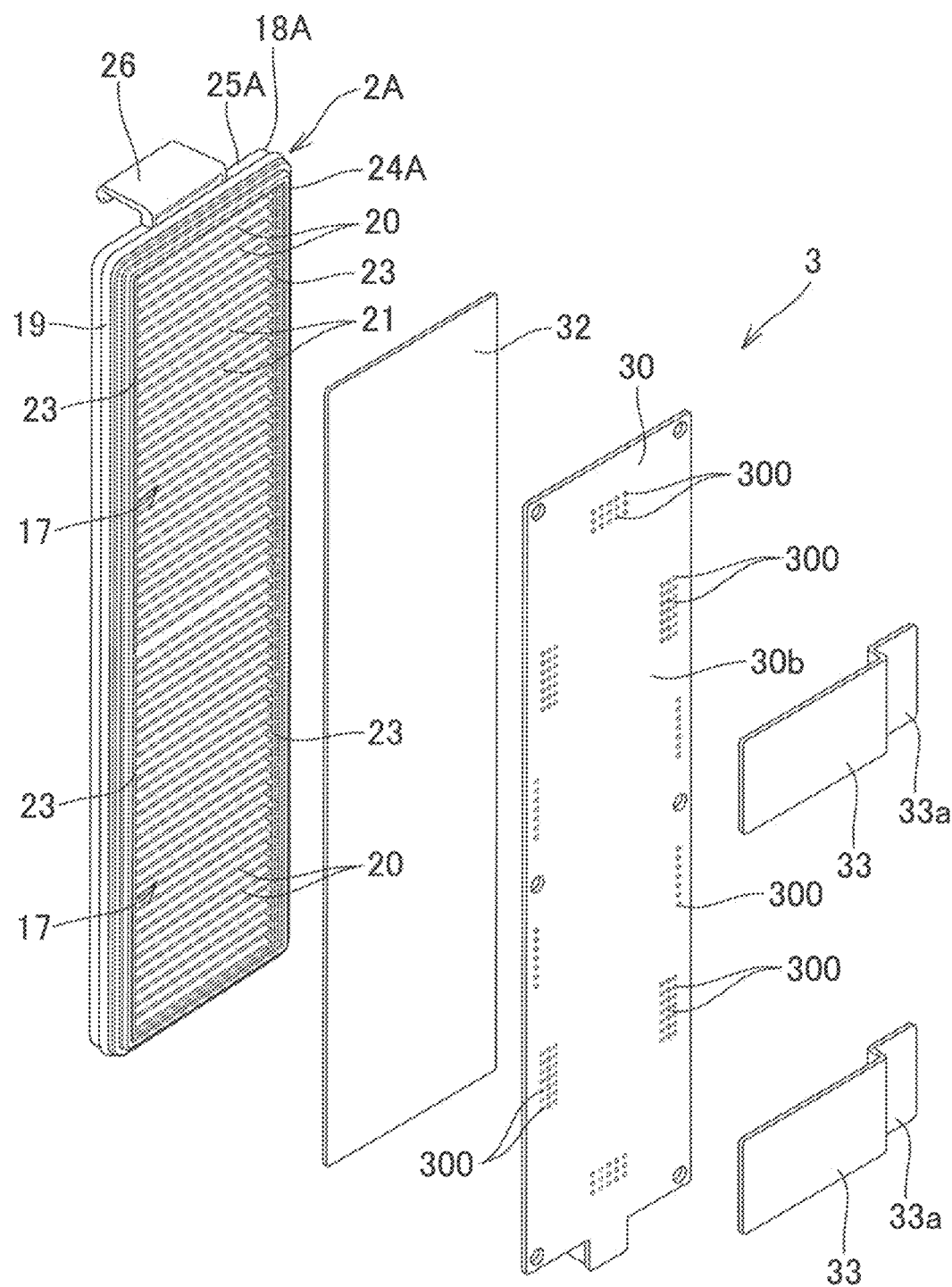
FIG. 20 is an exploded perspective view of a photocatalytic filter, a UV light source, and a cover plate.
Figure 21:
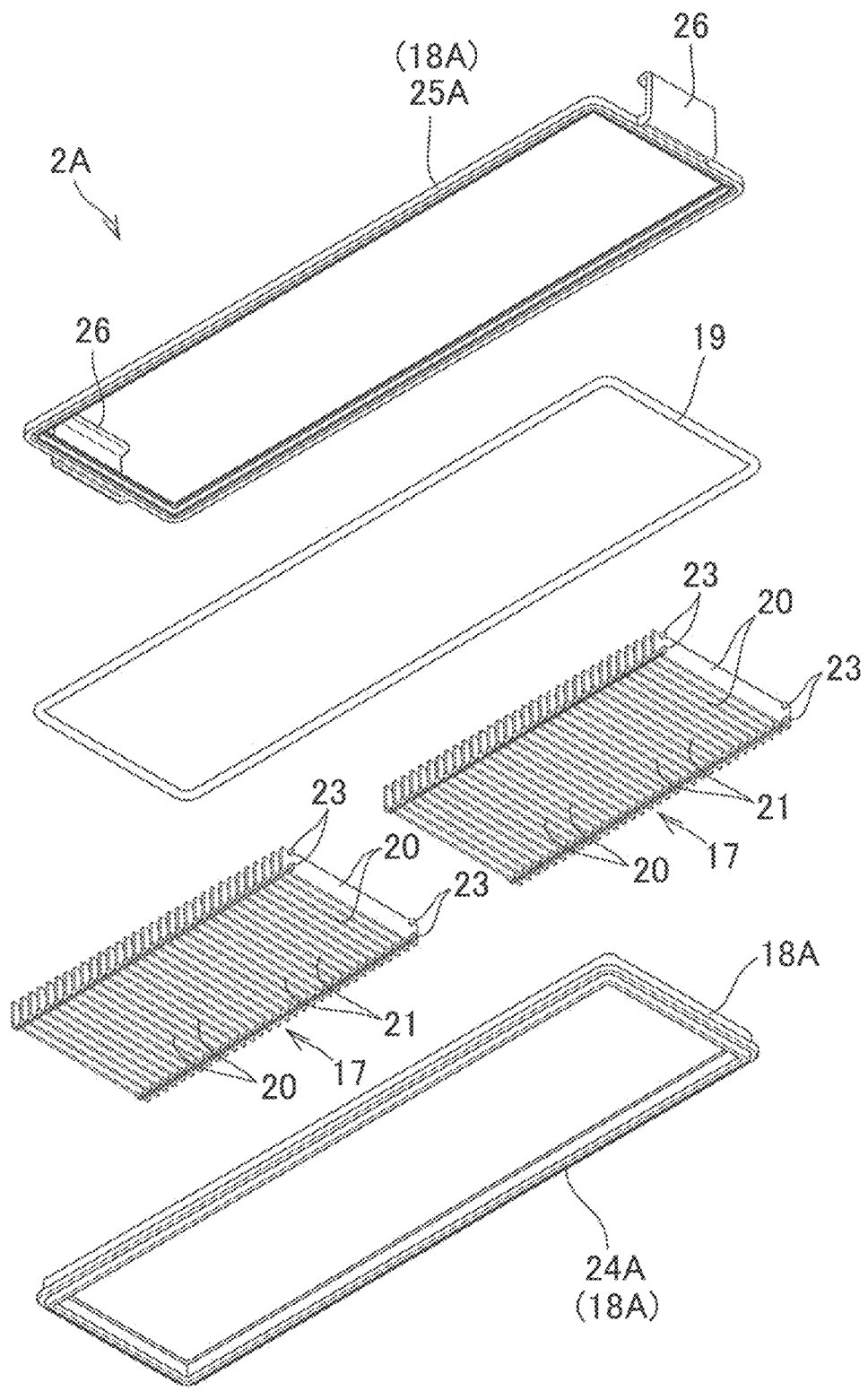
FIG. 21 is an exploded perspective view of the photocatalytic filter of FIG. 20.

In this example, as shown in FIGS. 20 and 21, each plate-shaped member 20 is formed of a flat plate instead of an undulating plate. As in the first embodiment, the plate-shaped members 20 are integrated together into a unit arrangement by four linking members 23. Such a unit arrangement is a metal filter base body 17. The metal filter base body 17 is fitted into a tube-shaped frame 18A formed of synthetic resin, to form the photocatalytic filter 2A.

As also shown in FIG. 18, the frame 18A of this example includes: a flat tube-shaped frame body 24A having a hook piece 24a on which a peripheral end portion of one (in this example, a surface on a side where the end surface 22b of each plate-shaped member 20 is positioned) of the surfaces in the thickness direction of the flat board-shaped metal filter base body 17 is hooked, the hook piece 24a being provided at an end in the axial direction of the flat tube-shaped frame body 24A; and a flat tube-shaped frame member 25A that is joined to the other end of the frame body 24A with a sealing member 19 being interposed therebetween, and has a hook piece 25b on which a peripheral end portion of the other surface (in this example, a surface on a side where the end surface 22a of each plate-shaped member 20 is positioned) of the metal filter base body 17 that is disposed inside the frame body 24A is hooked.

Figure 15:
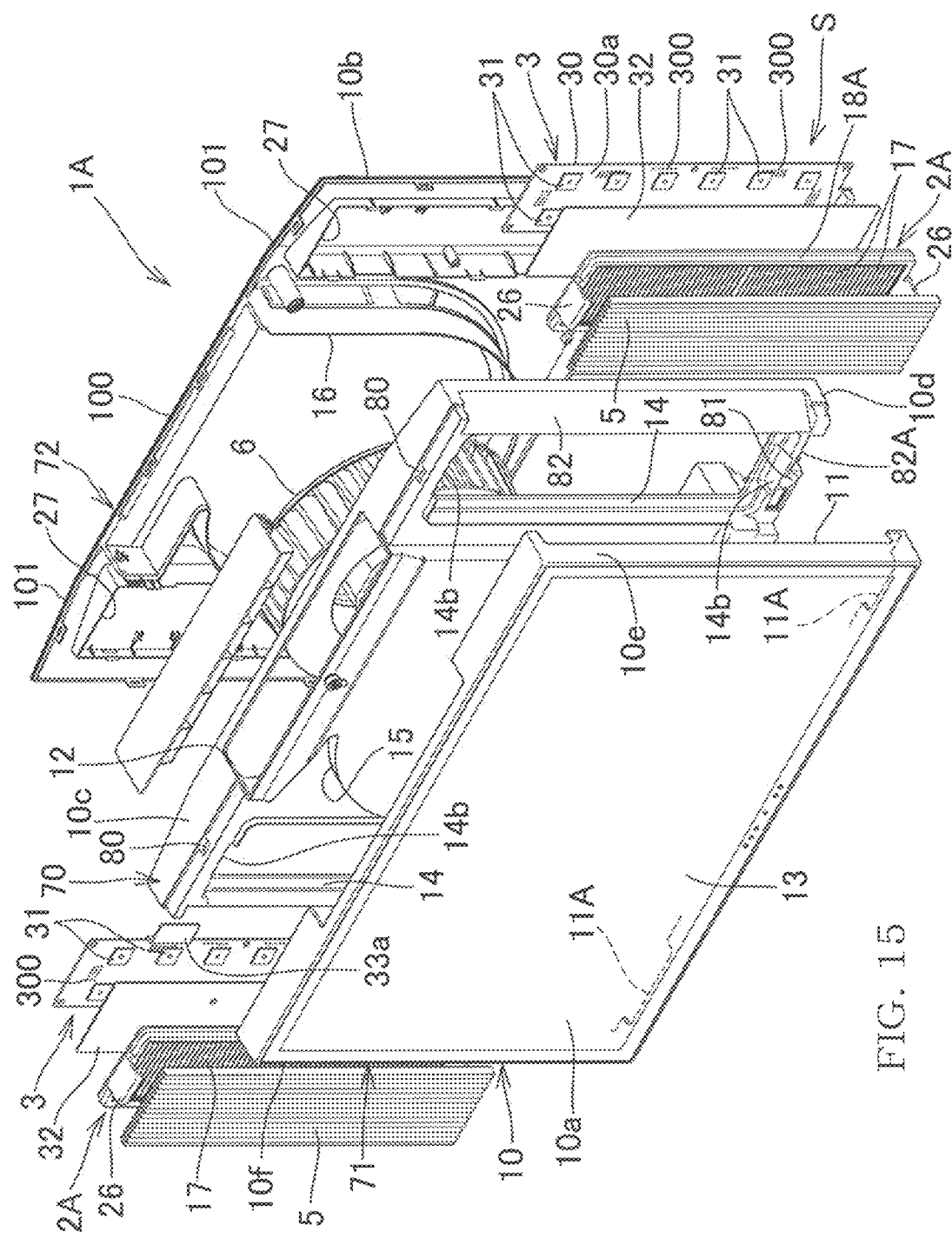
FIG. 15 is an exploded perspective view showing an air cleaner according to a second embodiment of the present invention.
Figure 24:
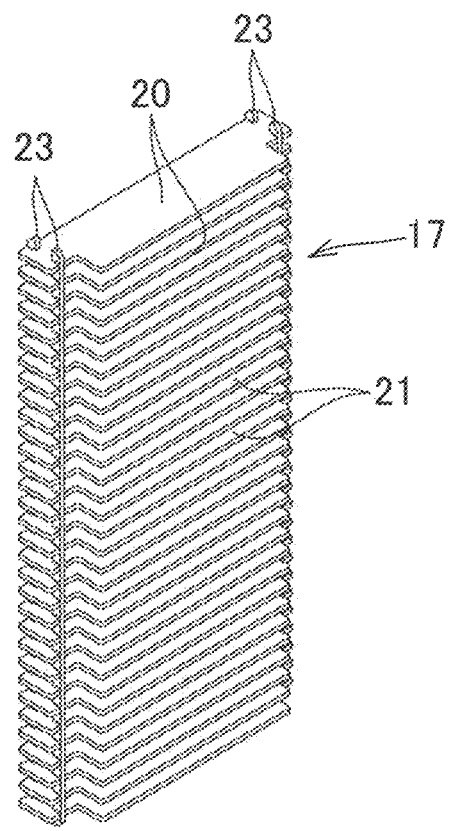
FIG. 24 is a perspective view showing a variation of a metal filter base body.
Figure 25:
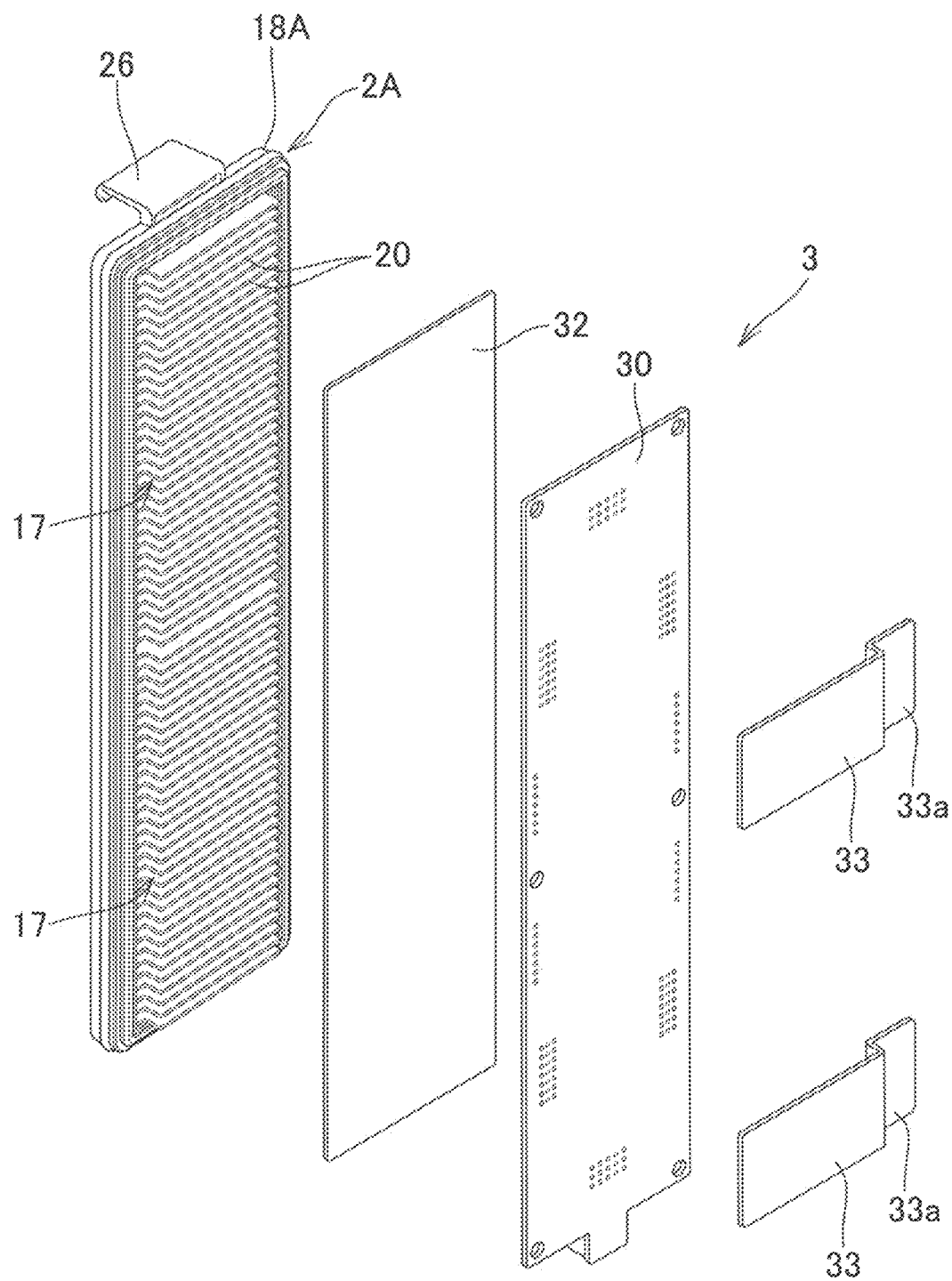
FIG. 25 is an exploded perspective view of a photocatalytic filter, a UV light source, and a cover plate, according to the variation of FIG. 24.
Figure 26:
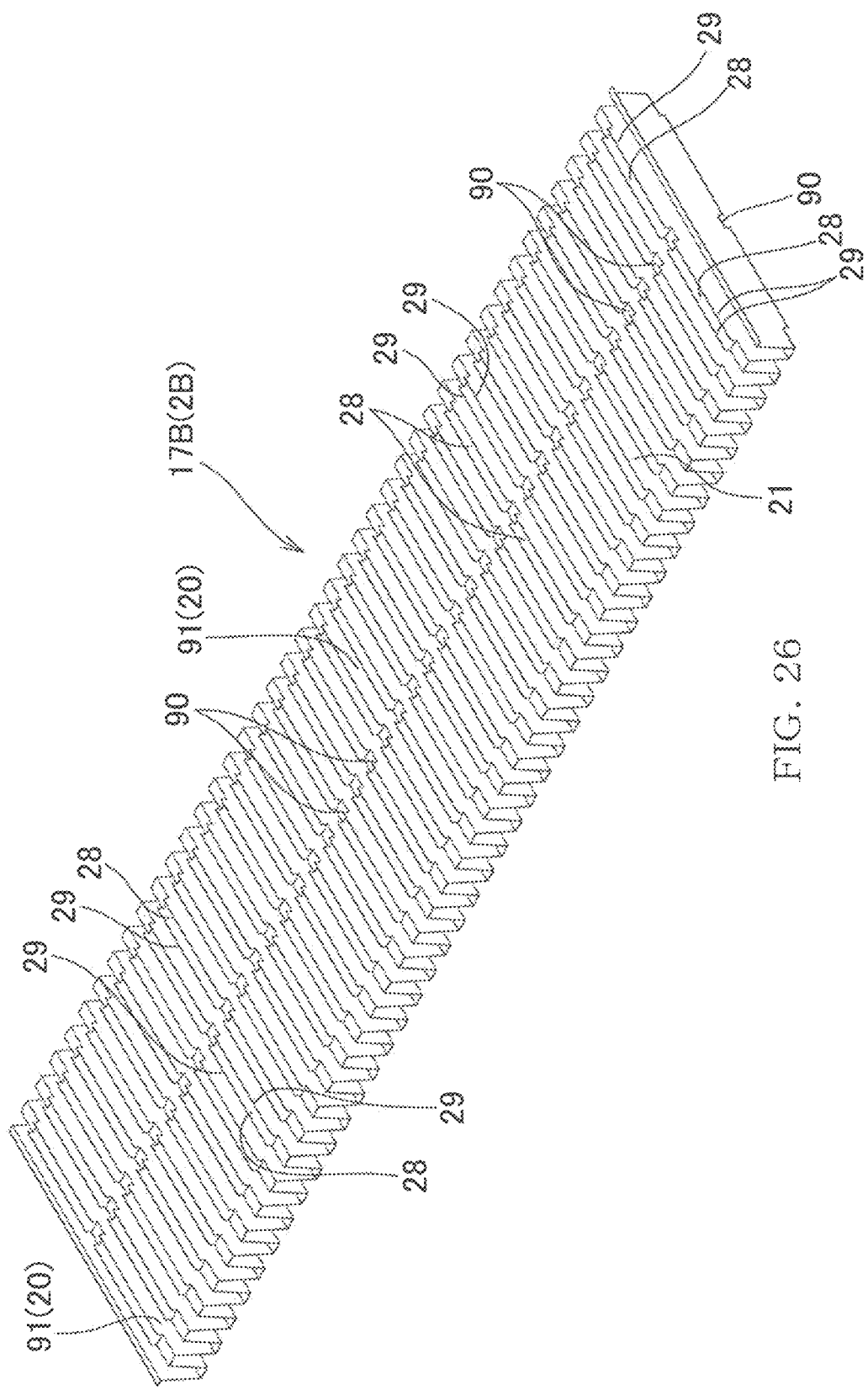
FIG. 26 is a perspective view showing a metal filter base body for use in a photocatalytic filter according to a third embodiment of the present invention.
Figure 27:
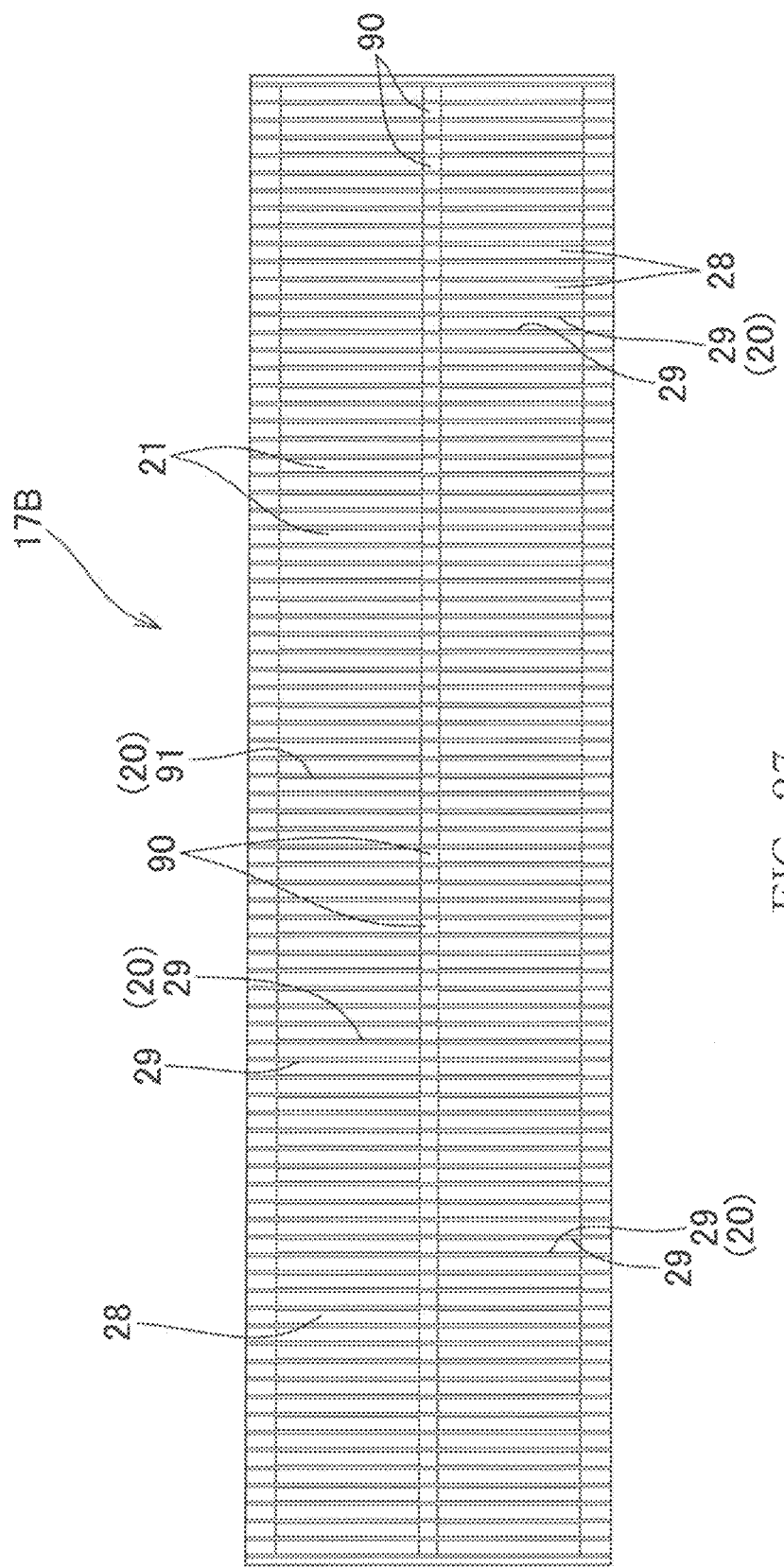
FIG. 27 is a front view of the metal filter base body of FIG. 26.
Figure 28:
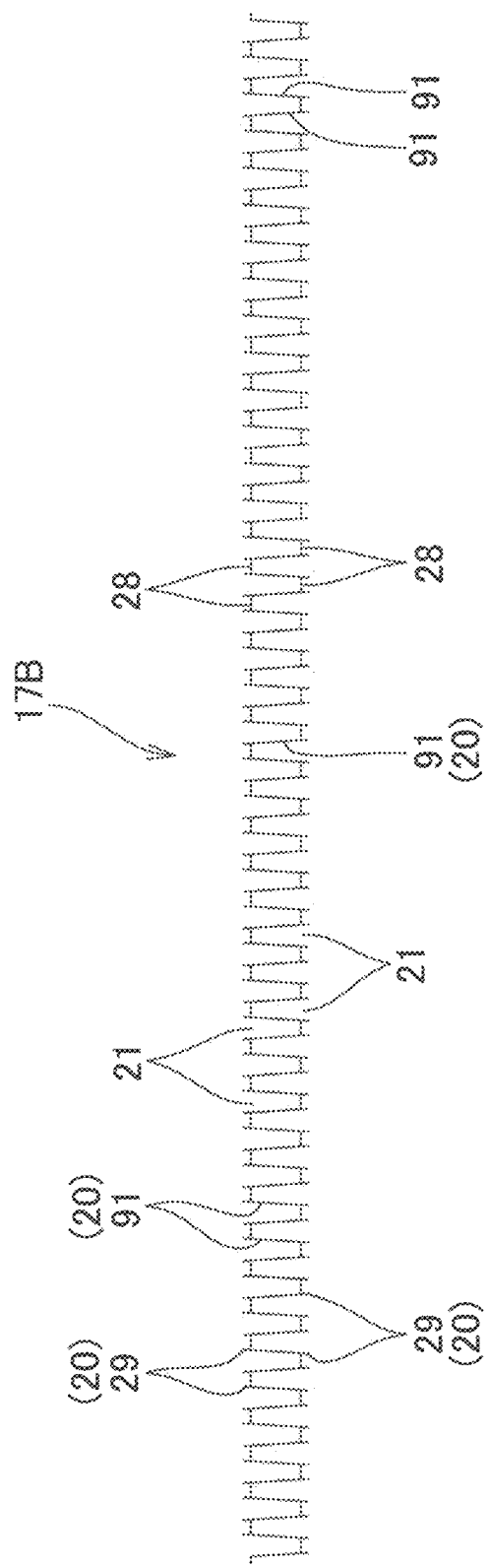
FIG. 28 is a side view of the metal filter base body of FIG. 26.
Figure 29:
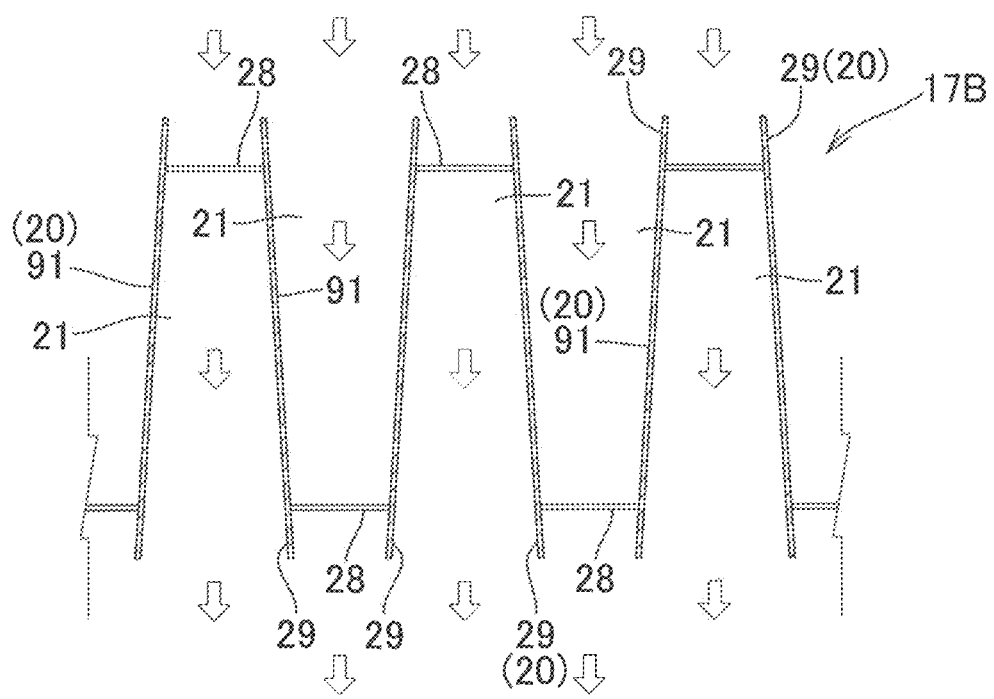
FIG. 29 is an enlarged cross-sectional view of a main portion of the metal filter base body of FIG. 26.
Figure 30:
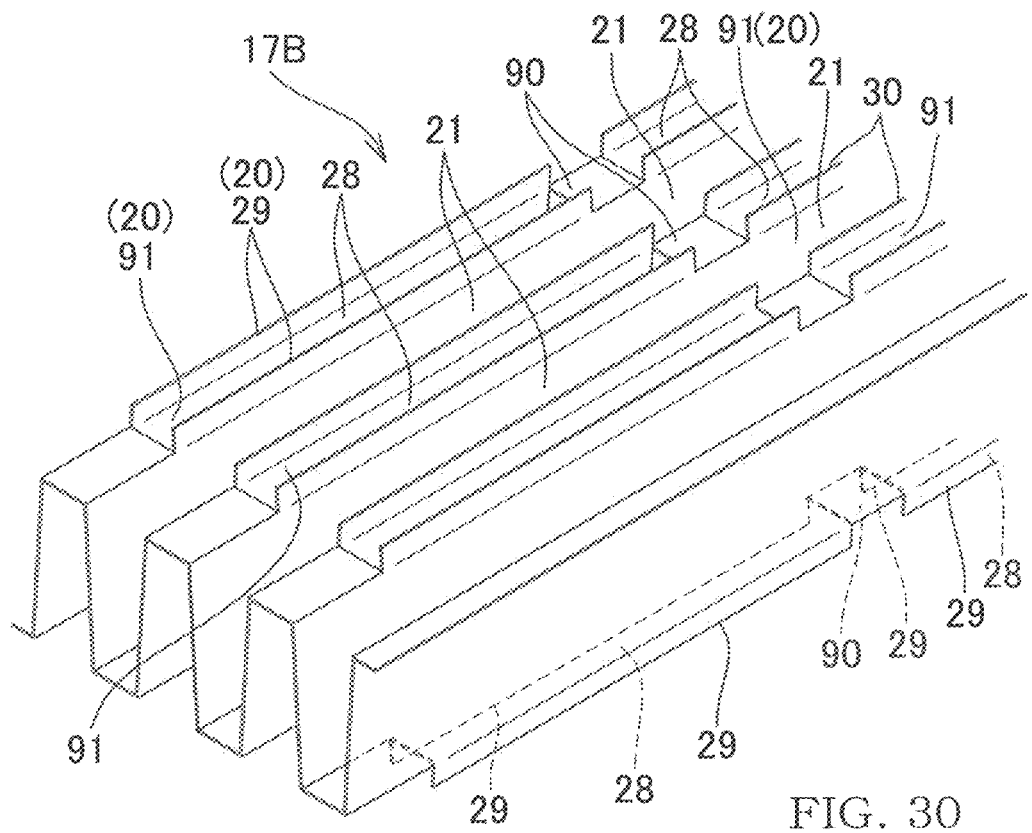
FIG. 30 is an enlarged perspective view of a main portion of the metal filter base body of FIG. 26.

The frame member 25A is provided with a lug 26 that is provided on the opposite side from the metal filter base body 17 and extends in the axial direction of the flat tube-shaped frame body 24A. As shown in FIGS. 15, 16, and 19, an engagement groove 14b with which the lug 26 is engaged is formed at a corresponding position in an inner surface of the frame part 14 to which the photocatalytic filter 2A is attached. The photocatalytic filter 2A can be easily removed from or attached to the frame part 14 with the lug 26 being held with a hand. Therefore, maintainability can be improved, and the dust collection filter 5 can be stably held by the lug 26. Each plate-shaped member 20 may undulate in the short side direction. Alternatively, for example, as shown in FIGS. 24 and 25, each plate-shaped member 20 may preferably have a convex outer shape in which a portion thereof at and around the center, excluding both end portions that are linked together by the linking members 23, protrudes on an end surface side facing the UV irradiation unit 3, and therefore, has an increased area.

Figure 22:
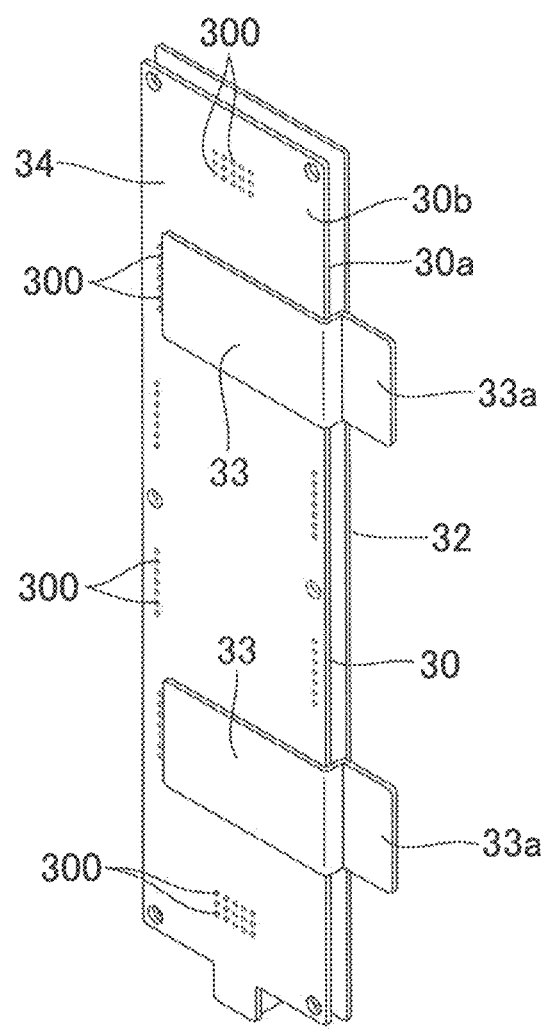
FIG. 22 is a perspective view of a UV light source and a cover plate as viewed from behind thereof.
Figure 23:
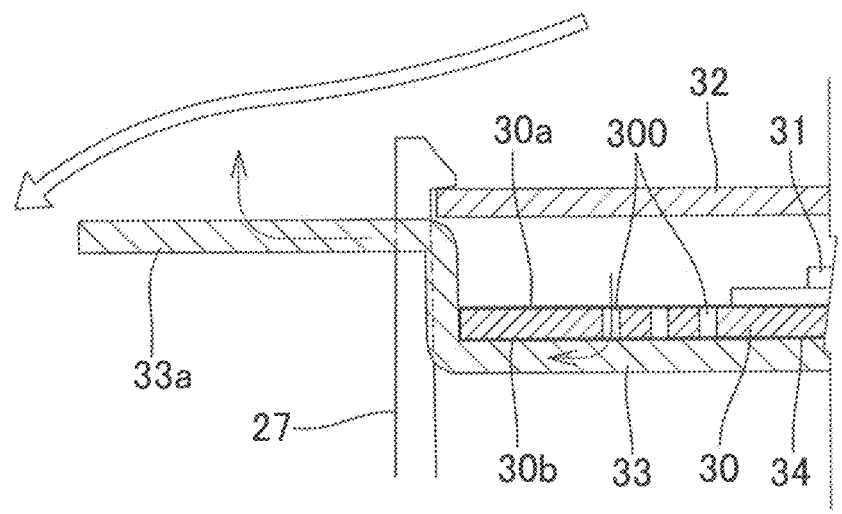
FIG. 23 is an explanatory diagram of main portions of a UV light source and a cover plate.

As shown in FIGS. 20 and 22, the substrate 30 included in the UV irradiation unit 3 is provided with a plurality of through holes 300. In addition, a heat dissipation metal plate 33 is fixed to the surface 30b of the substrate 30 opposite to the surface 30a on which the UV light source 31 is attached, with a portion of the metal plate 33 extending out laterally. As shown in FIGS. 18 and 23, the metal plate 33 is configured such that an extension portion 33a of the metal plate 33 penetrates through the frame part 27 to which the substrate 30 is attached, and protrudes in the air discharge path 42. Therefore, heat that occurs in the UV light source 31 and tends to reside between the UV light source 31 and the cover plate 32, can be transferred from the surface 30b of the substrate 30 to the metal plate 33, which in turn efficiently dissipates the heat from the extension portion 33a into air flowing in the air discharge path 42.

The through holes 300 thus formed can guide heat from a side where the surface 30a of the substrate 30 is positioned to a side where the opposite surface 30b is positioned. In particular, if the metal plate 33 is fixed such that all or a part of the through holes 300 are occluded, heat occurring on the side where the surface 30a is positioned can be directly transferred through the through holes 300 to the metal plate 33, which in turn dissipates the heat. In this example, a metal sheet 34 of aluminum, etc., is attached to at least the surface 30b of the substrate 30, and the metal plate 33 is fixed to the metal sheet 34, and therefore, heat is more easily transferred. In this case, the through holes 300 preferably also penetrate through the metal sheet 34.

The other configurations and variations of the air cleaner 1A employing the photocatalytic filter 2A according to this embodiment are substantially the same as those of the first embodiment, and therefore, the same parts are indicated by the same reference characters and will not be described.

Next, a third embodiment of the present invention will be described with reference to FIG. 26, FIG. 27, FIG. 28, FIG. 29, FIG. 30, FIG. 31, FIG. 32, FIG. 33 and FIG. 34.

In this embodiment, as shown in FIG. 26, FIG. 27, FIG. 28, FIG. 29 and FIG. 30, a photocatalytic filter 2B includes a metal filter base body 17B having a metal plate body in which row-shaped crest portions (ridges) and trough portions (furrows) are alternately formed. A through groove 28 extending in the row direction for passing a fluid is provided in both the crest portion and the trough portion. A middle wall portion 91 facing the through groove 28 is equivalent to the above plate-shaped member 20. A gap 21 between adjacent middle wall portions 91 and 91 (plate-shaped members 20 and 20) serves as an air flow path 41 to and from which air enters and exits through the through groove 28.

A photocatalyst is carried on at least a front and a rear surface of the middle wall portion 91. In this example, a photocatalyst is carried on the entire surfaces of the metal filter base body 17B. A raised strip 29 that is raised on a convex surface side of the crest portion or trough portion is provided at an opening edge portion of each of the through grooves 28 of the crest portions and trough portions of the metal filter base body 17B. The raised strip 29 and the middle wall portion 91 constitute the plate-shaped member 20.

Figure 31:
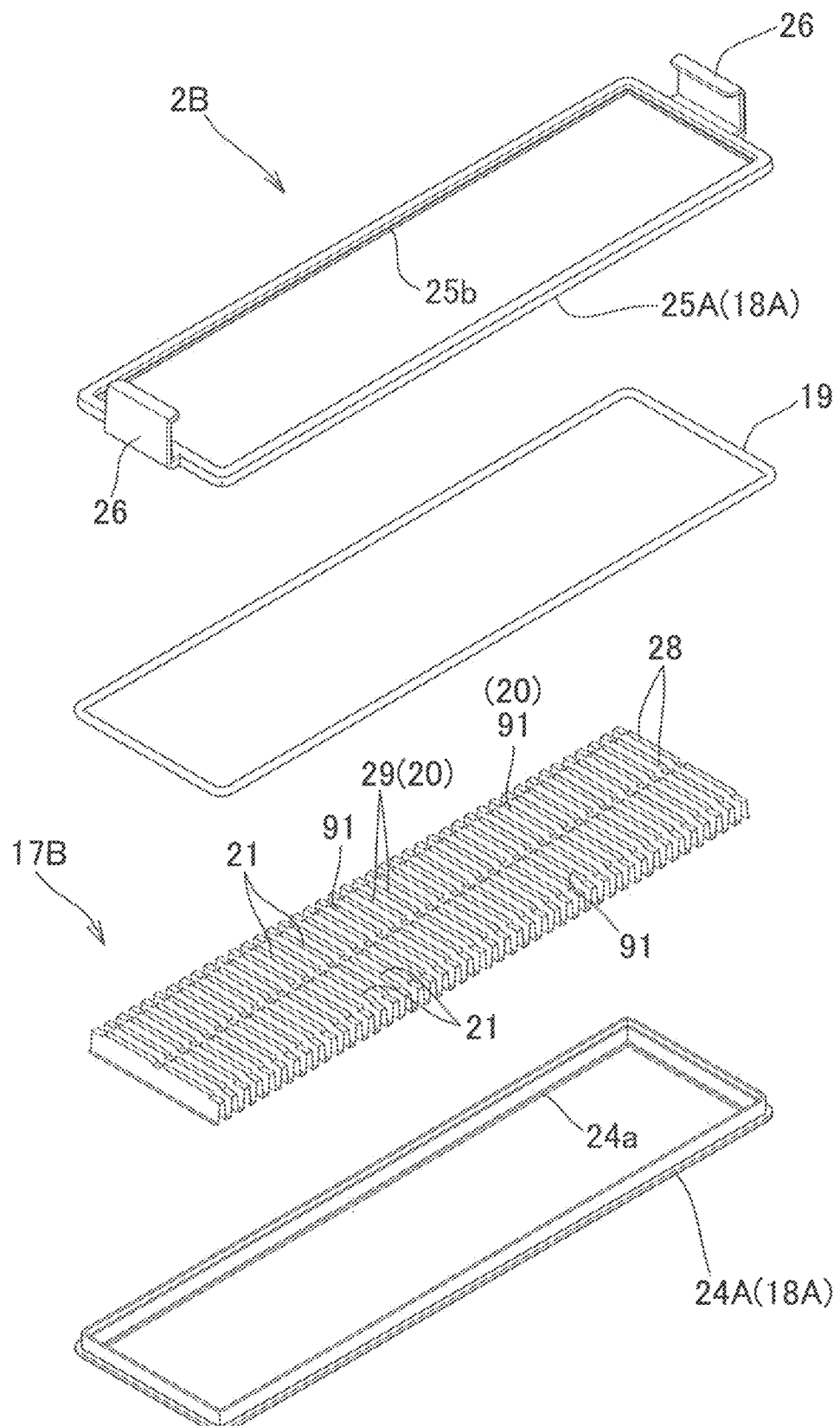
FIG. 31 is an exploded perspective view of a photocatalytic filter in connection with the metal filter base body of FIG. 26.
Figure 32:
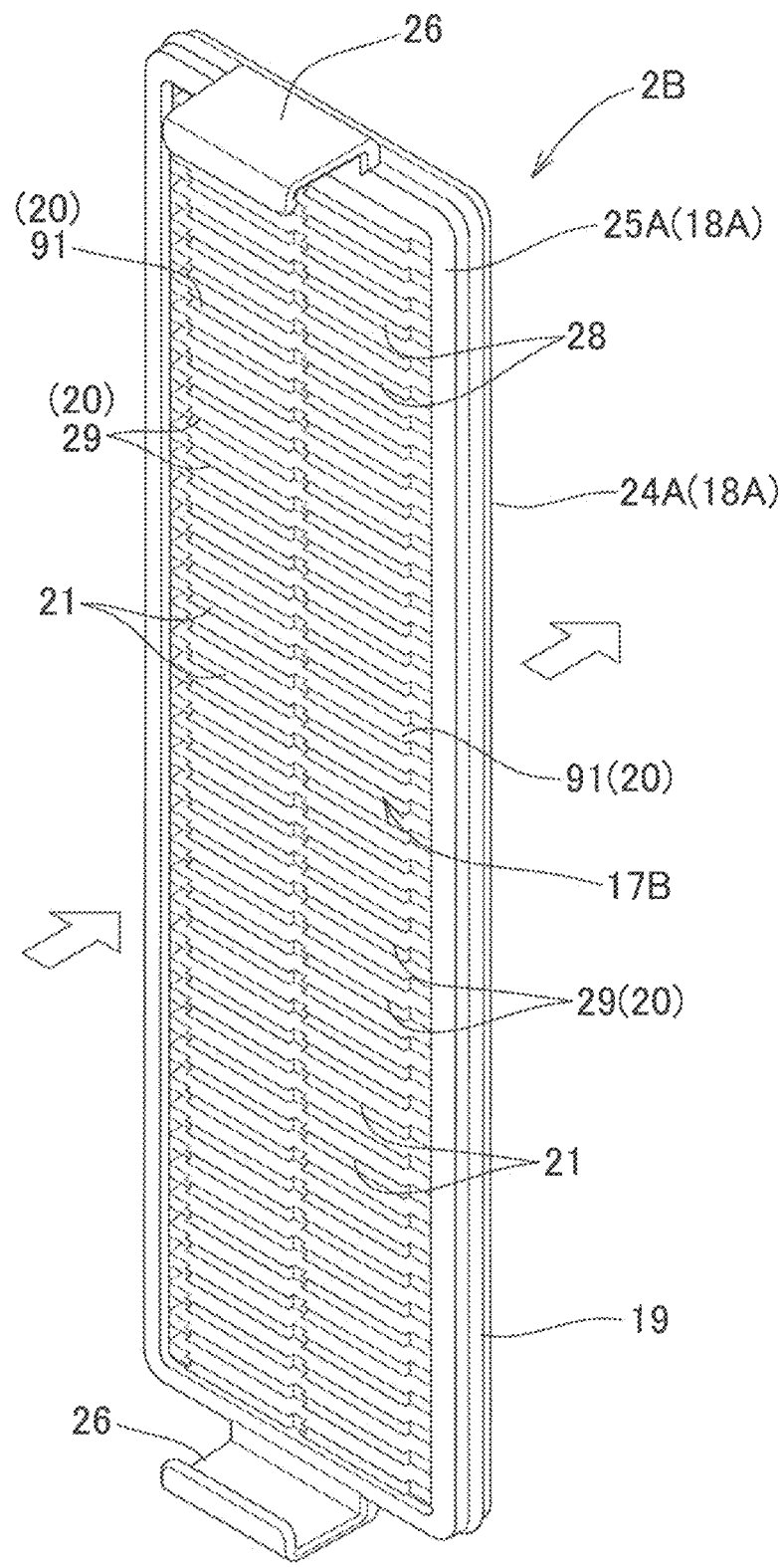
FIG. 32 is a perspective view of the photocatalytic filter of FIG. 31.
Figure 33:
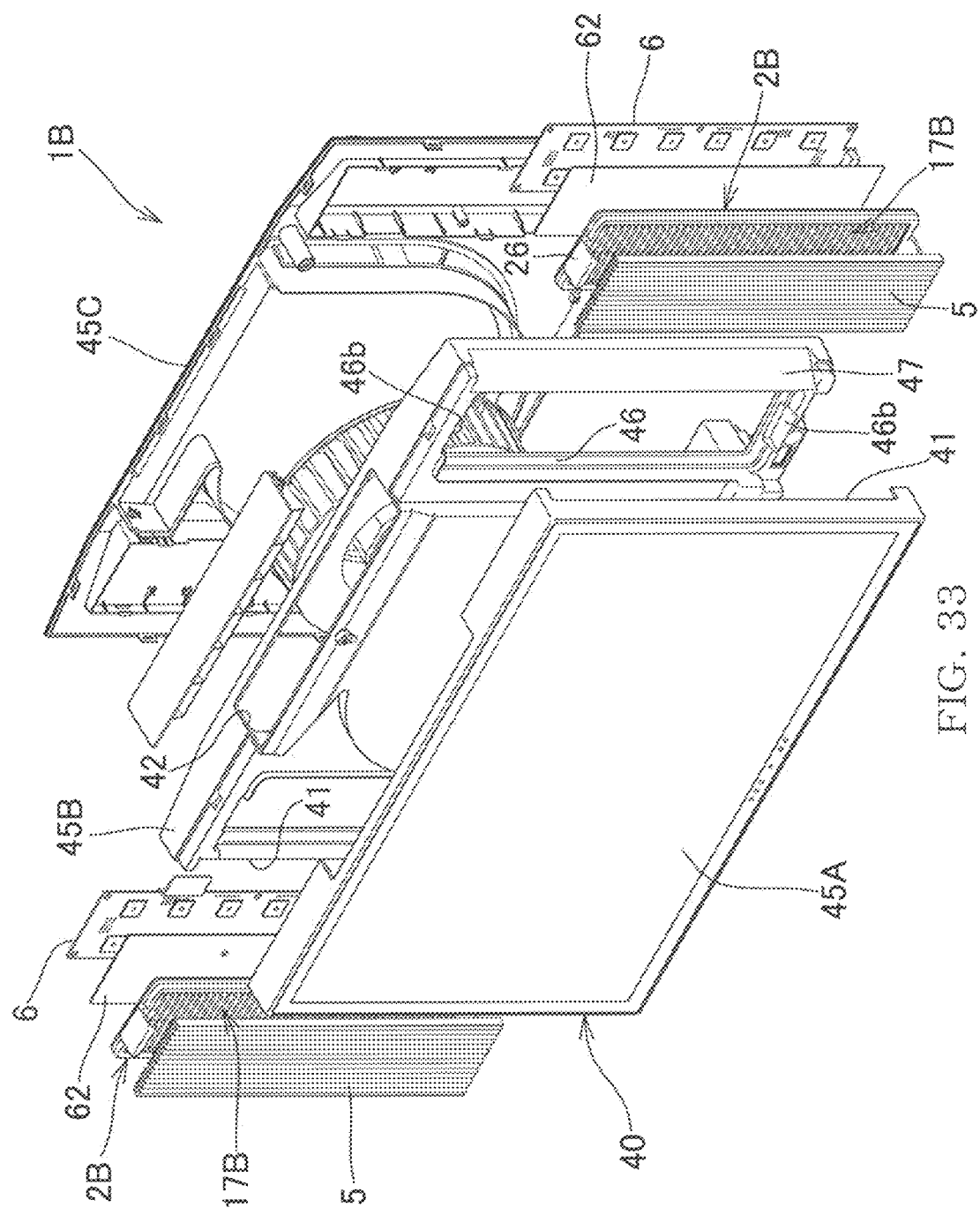
FIG. 33 is an exploded perspective view of an air cleaner employing the photocatalytic filter of FIG. 31.
Figure 34:
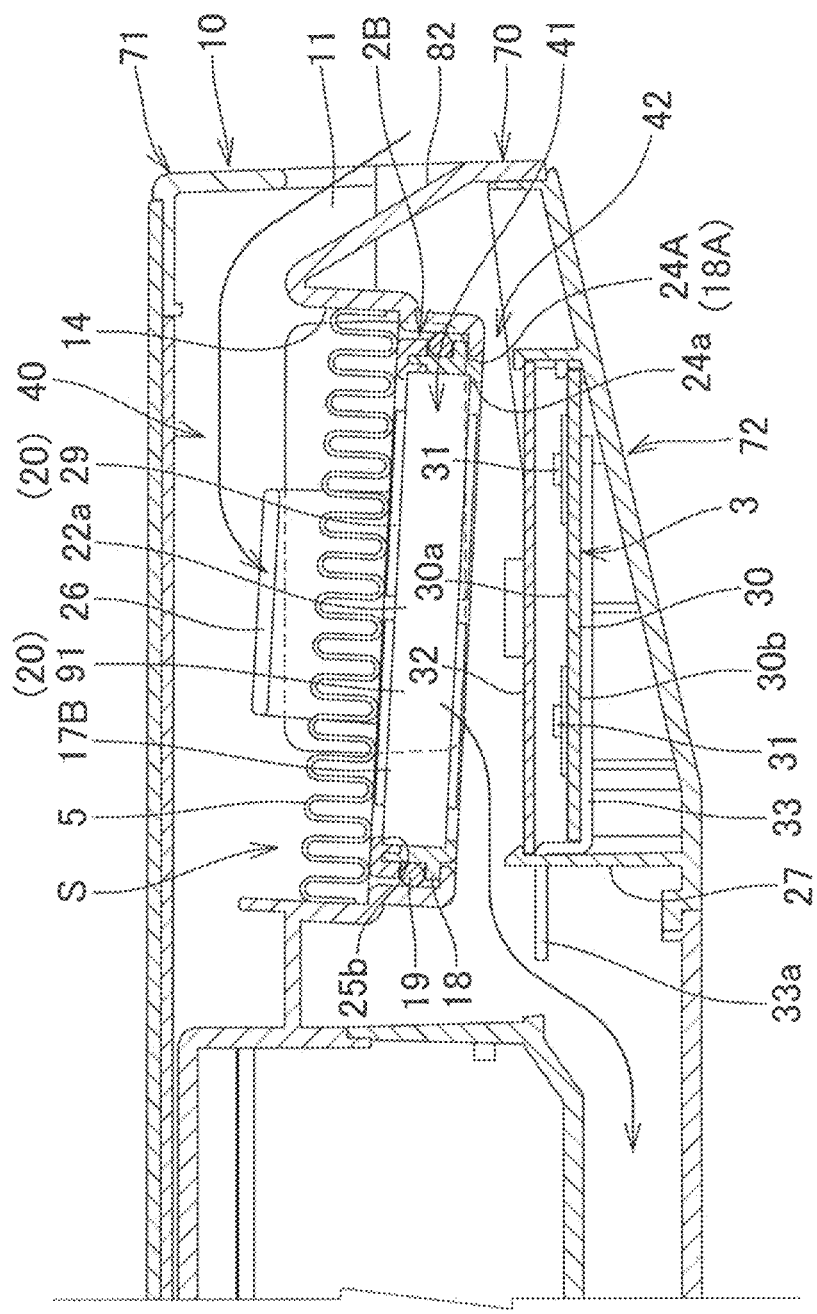
FIG. 34 is an enlarged explanatory diagram showing flow of air in the air cleaner of FIG. 33.

As shown in FIGS. 31 and 32, the metal filter base body 17B is fitted into a tube-shaped frame 18A formed of synthetic resin that has the same structure as that of the second embodiment, to form the photocatalytic filter 2B. Air passes through each through groove 28, moving one side to the other side.

The metal filter base body 17B thus configured has a large surface area where the metal filter base body 17B comes into contact with a fluid, due to a crest-and-trough surface formed by the crest portions and trough portions. In addition, an inner surface of the through groove 28 formed in the crest portion or trough portion, and the raised strip 29 provided at the opening edge portion thereof, contribute to an increase in the surface area where the metal filter base body 17B comes into contact with a fluid. Therefore, the catalytic effect of the photocatalyst can be efficiently exerted. The raised strip 29 does not interfere with passage of ultraviolet light, and therefore, a catalyst layer formed on surfaces of the middle wall portion 91 and the raised strip 29 is efficiently irradiated with ultraviolet light.

The crest-and-trough shape formed by the crest portions and trough portions, and the raised strips 29 can be formed by pressing at low cost. In particular, the raised strips 29 can be efficiently formed by a cutting-and-raising process employing punching, simultaneously with or immediately after pressing for forming the crest-and-trough shape. It would be obvious that the present invention is not limited to these processing methods and procedures. In the case of the metal filter base body 17B of this embodiment, unlike the metal filter base body 17 of the first and second embodiment, it is not necessary to perform the step of fixing a plurality of plate-shaped members 20 to the linking member 23 by crimping, etc., so that the plate-shaped members 20 and the linking member 23 are integrated together. Therefore, even if the metal filter base body 17B is formed of a thinner plate, the strength can be maintained, resulting in a significant reduction in manufacturing cost and material cost.

In this example, the crest portions and the trough portions are each formed into a squared shape by bending such that the crest portions and the trough portions as a whole form a crest-and-trough shape. Alternatively, the crest portions and the trough portions may be formed into a continuous, gentle curved shape by bending. Concerning the "crest portion" and the "trough portion", in the case where one of crest and trough surfaces of a crest-and-trough shape is referred to as a front side, and the other is referred to as a rear surface, the "crest portion" is defined as a portion of the crest-and-trough shape that protrudes in the front surface side, and the "trough portion" is defined as a portion of the crest-and-trough shape that protrudes in the rear surface side.

In this example, in each crest portion or trough portion, two elongated through grooves 28 extending in the row direction are arranged in a row with a space being interposed therebetween. A bridge portion 90 is formed between the through grooves 28 (a remaining portion between the through grooves 28 in the crest portion or the trough portion). This structure as a whole can maintain shape retentivity. The lengths and space of the through grooves 28 can be determined, as appropriate, according to the thickness of the plate, other dimensions, and the degree of required shape retentivity. For example, three or more through grooves 28 may be provided in a row in the row direction, or only a single through groove 28 may be provided.

The raised strip 29 is configured to be provided at each of the pair of opening edge portions facing each other across the through groove 28 and extending in the row direction, and to efficiently come into contact with a fluid passing through the through groove 28, at both of the opening edge portions. Alternatively, it would be obvious that the raised strip 29 can be provided at only one of the opening edge portions. In the case of cutting-and-raising, the raised strip 29 formed at only one of the opening edge portions can have a long protrusion length.

Although it is assumed above that the raised strips 29 individually provided at each of the opening edge portions are an elongated strip extending along substantially the full length of each opening edge portion, a plurality of raised strips may be provided with a space being interposed between each raised strip. In this case, raised strips having a long protrusion length can be formed at both of the opening edge portions alternately (in a staggered pattern) by cutting-and-raising.

The raised strip 29 is a cut-and-raised strip as described above. A strip that is separately formed can be attached by brazing, etc. The cut-and-raised strip can be efficiently formed by mechanical processing at low cost. Specifically, a slit is made in the crest portion or the trough portion along a center thereof, and strips on both sides of the slit are raised, to form the raised strip 29. As a result, the through groove 28 is formed.

When the raised strip 29 is thus formed by cutting-and-raising, the base material can be used while minimizing waste, and the contact area can be maximized. The raised strip 29 protrudes and is substantially flush with the middle wall portion 91 linking the crest portion and the trough portion. Specifically, the raised strip 29 and the through groove 28 are formed by cutting and raising the top surface (bottom surface) of the crest portion (trough portion) across the entire width such that there is not a step or a difference in level between the through groove 28 and the middle wall portion 91. Therefore, passage resistance on passing air is minimized, so that the pressure loss of the air is reduced, and therefore, the air can be efficiently cleaned.

The other configurations and variations of the air cleaner 1B employing the photocatalytic filter 2B according to this embodiment are substantially the same as those of the first or second embodiment, and therefore, the same parts are indicated by the same reference characters and will not be described.

Figure 36:
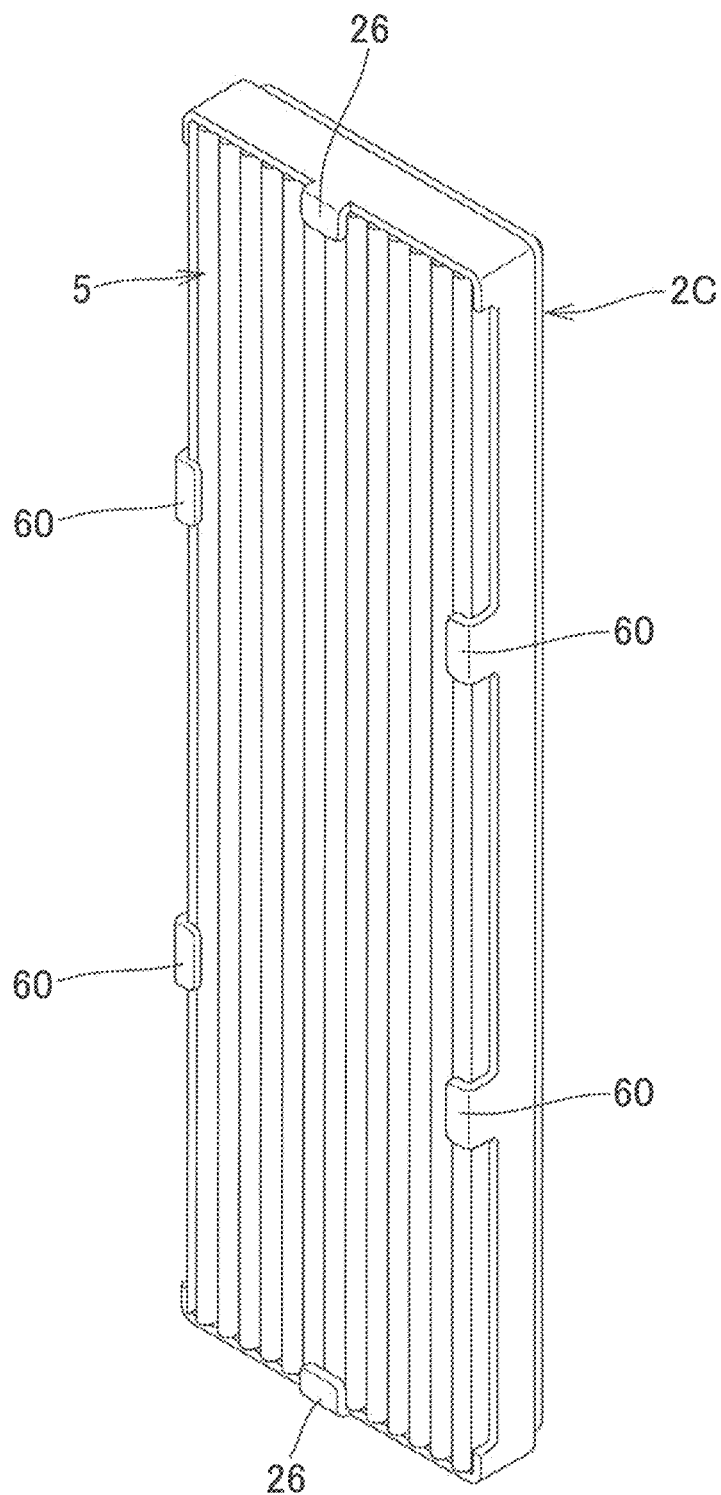
FIG. 36 is a perspective view showing an arrangement in which a dust collection filter is joined to the photocatalytic filter of FIG. 35.
Figure 37:
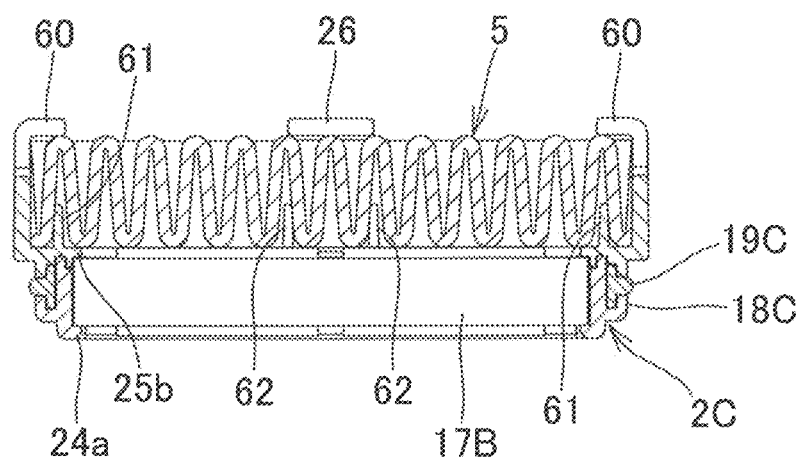
FIG. 37 is a horizontal cross-sectional view showing an arrangement in which a dust collection filter is joined to the photocatalytic filter of FIG. 35.

Next, a fourth embodiment of the present invention will be described with reference to FIG. 35, FIG. 36 and FIG. 37.

Figure 35:
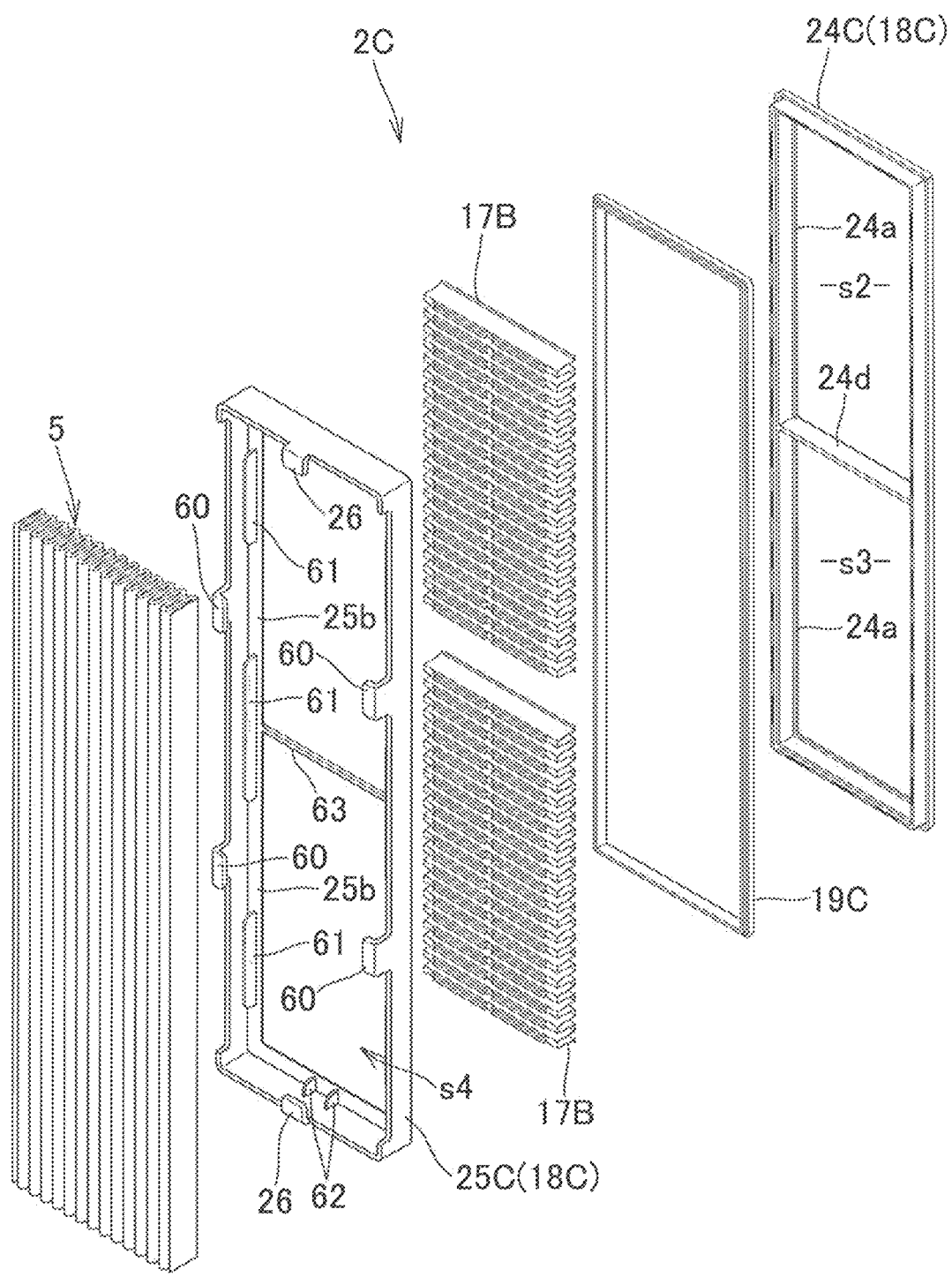
FIG. 35 is an exploded perspective view of a photocatalytic filter according to a fourth embodiment of the present invention.

As shown in FIG. 35, in this embodiment, a frame 18C for a photocatalytic filter 2C includes a flat tube-shaped frame body 24C having an accommodation space s2 and an accommodation space s3 each for accommodating the metal filter base body 17B, and a flat tube-shaped frame member 25C that is attached to the frame body 24C with a sealing member 19C being interposed therebetween, and has an accommodation space s4 for accommodating the dust collection filter 5. As a result, as shown in FIGS. 36 and 37, the dust collection filter 5 is stably held in the frame member 25C. Therefore, when integrally attached or removed, together with the photocatalytic filter 2C, to or from the frame part 14, the dust collection filter 5 is maintained in a stable position without coming off during the attachment or removal work, resulting in good workability.

In this example, the frame body 24C is divided into two portions in the vertical direction by a partition plate 24d, to form the above two accommodation spaces s2 and s3. Two of the metal filter base bodies 17B illustrated in the third embodiment, which are separate, are attached to, i.e., fitted into, the respective accommodation spaces s2 and s3. A hook piece 24a on which the metal filter base body 17B is hooked is provided and protrudes on an inner surface of an end portion of the frame body 24C, which is opposite to a surface of the end portion facing the frame member 25C. The partition plate 24d improves the strength of the frame body 24C.

A hook piece 25b on which the metal filter base bodies 17B are hooked is provided and protrudes on an inner surface of an end portion of the frame member 25C facing the frame body 24C, in a manner of extending all around the frame member 25C. The metal filter base bodies 17B are held in the frame body 24C with the metal filter base bodies 17B being sandwiched by the hook piece 25b and the hook piece 24a of the frame body 24C. The hook piece 25b of the frame member 25C also has the function of hooking the dust collection filter 5 accommodated and held in the accommodation space s4, by the other surface, i.e., an inner surface of the hook piece 25b, which faces the accommodation space s4 of the frame member 25C.

Fastening pieces 60 for fastening the dust collection filter 5, and lugs 26 are provided and protrude on an end portion of the frame member 25C on a side thereof that is opposite to a side thereof facing the frame body 24C, to hold the dust collection filter 5 in a stable position. Fastening hooks 61 and 62 that are fitted into a recessed surface of the corrugated dust collection filter 5 to fasten the dust collection filter 5 in an expanded state, are provided and protrude on a surface of the hook piece 25b that abuts on the dust collection filter 5.

Thus, the dust collection filter 5 is held in the accommodation space s4 with the dust collection filter 5 being expanded without shrinking, and therefore, the function of the dust collection filter 5 is maintained. In particular, when a photocatalyst is carried by the dust collection filter 5, the photocatalyst is efficiently irradiated with light, and therefore, the photocatalytic function is maintained. A reinforcing rod 63 is provided on the inner surface of the end portion of the frame member 25C, which faces the frame body 24C, at a position corresponding to the partition plate 24d of the frame body 24C, in a manner of spanning across the accommodation space s4, thereby improving the strength of the frame member 25C.

The other configurations and variations of the air cleaner employing the photocatalytic filter 2C according to this embodiment are substantially the same as those of the first, second, or third embodiment, and therefore, the same parts are indicated by the same reference characters and will not be described.

While embodiments of the present invention have been described, it would be obvious that the present invention is in no way limited to the embodiments, and the present invention can be carried out in various embodiments without departing from the spirit and scope of the present invention.

DESCRIPTION OF THE REFERENCE CHARACTERS 1, 1A, 1B air cleaner
2, 2A, 2B, 2C photocatalytic filter
3 UV irradiation unit
5 dust collection filter
6 fan
7 odor sensor
10 housing
10a front wall
10b rear wall
10c upper wall
10d lower wall
10e right wall
10f left wall
11, 11A intake opening
12 discharge opening
13 display unit
14 frame part
14b engagement groove
15 partition wall
16 partition wall
17, 17B metal filter base body
18, 18C frame
19, 19C sealing member
20 plate-shaped member
21 gap
22a end surface
22a, 22b end surface
22c recessed notch
23 linking member
23a recessed portion
24, 24C frame body
24a hook piece
24b recessed notch
24c recessed groove
24d partition plate 25, 25C frame plate
25a protrusion
25b hook piece
26 lug
27 frame part
28 through groove
29 raised strip
30 substrate
30a, 30b surface
31 UV light source
32 cover plate
33 metal plate
33a extension portion
34 metal sheet
40, 40A air supply path
41 flow path
42 air discharge path
51 first filter layer
52 second filter layer
60 fastening piece
61, 62 fastening hook
63 reinforcing rod
70 base body part
71 front cover part
72 rear cover part
73 opening
74 wall-mount member
80 fastening recessed portion
81 insertion hole
82, 82A guide wall
90 bridge portion
91 middle wall portion
100 middle portion
101 side portion
300 through hole
S air cleaning structure
W wall surface
s1 gap
s2 to s4 accommodation space

The invention claimed is:

1. A photocatalytic air cleaning structure for use in an air cleaner comprising:
a photocatalytic filter that includes a plurality of plate-shaped members each having a front and a back surface carrying a photocatalyst and being arranged such that the front surface of one plate-shaped member faces the back surface of another plate-shaped member adjacent thereto with a gap being interposed therebetween, the gap defining an air flow path for air flowing along the front surface and the back surface of the plate-shaped members adjacent to each other, and a metal filter base body that includes a metal plate body having a plurality of crest portions and a plurality of trough portions alternately formed, with a through groove extending in a row direction for allowing a fluid to pass through being provided in each of the crest portions and each of the trough portions; and a middle wall portion facing the through groove being one of the plate-shaped members, the plate-shaped members extending in parallel, and the plate-shaped members being connected to the crest portions and trough portions; and
a UV irradiation unit that emits ultraviolet light toward the gap, and faces one of end surfaces of each of the plate-shaped members of the photocatalytic filter with a predetermined distance array from the one of the end surfaces, the end surfaces including an end surface on an air entrance side to the gap and an end surface on an air exit side from the gap, wherein;
the UV irradiation unit and one of the end surfaces of the plate-shaped member are arranged so as to define therebetween: an air supply path for taking in air from a lateral direction substantially parallel to the one of the end surfaces, and supplying the air to the air flow path defined by the gap between the plate-shaped members; or an air discharge path for discharging the air exiting from the flow path to a lateral direction substantially parallel to the one of the end surfaces, the air discharge path passing through the space between the photocatalytic filter and the UV irradiation unit, the end surfaces of the plate-shaped members extending in the same direction as the crest portions and trough portions, and
the gap, which has an elongated plate shape between the plate-shaped members each having a flat shape, continuously extends in a direction along the end surfaces of the plate-shaped members, the gap extending in the same direction as the crest portions and the trough portions.

2. The photocatalytic air cleaning structure according to claim 1, wherein
each of the plate-shaped members of the photocatalytic filter has a pair of short sides facing each other and a pair of long sides facing each other,
the end surface on the air entrance side and the end surface on the air exit side are the end surfaces corresponding to the pair of long sides of each of the plate-shaped members, thereby allowing air to pass through the air flow path in a direction in which the short sides of the plate shaped members extend, and
the UV irradiation unit is positioned to face the end surfaces corresponding to at least one of the pair of long sides of the plate-shaped member.

3. The photocatalytic air cleaning structure according to claim 1, wherein
the air supply path or the air discharge path is a flow path defined between the UV irradiation unit and the end surfaces on the at least one of the air entrance and exit sides of the plate-shaped members, the flow path allowing air to be taken from or discharged to a lateral direction which is substantially parallel to the end surfaces on the at least one of the air entrance and exit sides, and corresponds to a direction in which the end surfaces on the at least one of the air entrance and exit sides extend.

4. The photocatalytic air cleaning structure according to claim 1, wherein
each of the plate-shaped members of the photocatalytic filter is an undulating plate that alternately bends toward front and back of the plate, in a direction along which the end surfaces on the air entrance side or the end surfaces on the air exit side extend.

5. The photocatalytic air cleaning structure according to claim 1, wherein
the UV irradiation unit is positioned to face the end surface on the air exit side of the plate-shaped member of the photocatalytic filter, and
a dust collection filter having a substantially white color is provided on the air entrance side of the photocatalytic filter so as to occlude an entrance of the air.

6. The photocatalytic air cleaning structure according to claim 5, wherein
a photocatalyst is carried by the dust collection filter.

7. The photocatalytic air cleaning structure according to claim 1, wherein the UV irradiation unit includes:
a substrate facing an entire of an air exit of the photocatalytic filter with a space being interposed therebetween, the space being the air discharge path;
a UV light source provided on and attached to a surface of the substrate, which faces the photocatalytic filter, and for irradiating the gap between the plate-shaped members with ultraviolet light; and
a light transmissive cover plate provided between the substrate and the photocatalytic filter, and
the air exiting from the gap between the plate-shaped members is discharged through the space between the cover plate and the end surface on the air exit side of each of the plate-shaped members, along a surface of the cover plate, toward a lateral edge.

8. The photocatalytic air cleaning structure according to claim 1, wherein
the photocatalytic filter includes a linking member for linking the plate-shaped members together, and all the plate-shaped members are integrated together into a unit arrangement by the linking member.

9. The photocatalytic air cleaning structure according to claim 1, wherein
each of the plate-shaped members is a metal plate.

10. An air cleaner comprising:
the photocatalytic air cleaning structure according to claim 1, wherein
in a housing, the photocatalytic filter and the UV irradiation unit facing the photocatalytic filter are positioned and aligned with each other in a fore-and-aft direction of the housing,
an air intake opening and an air discharge opening are each provided in an upper, a lower, a left, and a right peripheral wall for linking a front and a rear wall of the housing at a predetermined position,
in the housing, the air supply path extending from the air intake opening to the air entrance of the photocatalytic filter, and an air discharge path extending from the air exit of the photocatalytic filter to the air discharge opening, are provided, and
a fan for forcing air to flow is provided in a middle of the air supply path or the air discharge path.

11. A photocatalytic filter for use in the air cleaning structure according to claim 1, wherein
the metal filter base body and the tube-shaped frame form a unit arrangement.

\* \* \* \* \*